United States Patent
Sockel et al.

(10) Patent No.: US 7,390,479 B2
(45) Date of Patent: Jun. 24, 2008

(54) BRANCHED POLYORGANOSILOXANE POLYMERS

(75) Inventors: Karl-Heinz Sockel, Leverkusen (DE); Karl-Heinz Stachulla, Leverkusen (DE); Anita Witossek, Langenfeld (DE); Roland Wagner, Bonn (DE)

(73) Assignee: GE Bayer Silicones GmbH & Co. KG, Leverkusen (DE)

( * ) Notice: Subject to any disclaimer, the term of this patent is extended or adjusted under 35 U.S.C. 154(b) by 230 days.

(21) Appl. No.: 10/507,551

(22) PCT Filed: Mar. 19, 2003

(86) PCT No.: PCT/EP03/02861

§ 371 (c)(1), (2), (4) Date: Jun. 3, 2005

(87) PCT Pub. No.: WO03/078504

PCT Pub. Date: Sep. 25, 2003

(65) Prior Publication Data

US 2005/0255073 A1   Nov. 17, 2005

(30) Foreign Application Priority Data

Mar. 20, 2002 (DE) ............................... 102 12 470

(51) Int. Cl.
*C08G 77/452* (2006.01)
*C08G 77/46* (2006.01)
*A61Q 5/00* (2006.01)

(52) U.S. Cl. .................. 424/70.12; 528/25; 528/27; 528/38

(58) Field of Classification Search ............... None
See application file for complete search history.

(56) References Cited

U.S. PATENT DOCUMENTS

| | | | |
|---|---|---|---|
| 4,417,066 A | 11/1983 | Westall | 556/425 |
| 4,533,714 A * | 8/1985 | Sebag et al. | 528/27 |
| 4,661,577 A | 4/1987 | Jo Lane et al. | 528/10 |
| 4,833,225 A | 5/1989 | Schaefer et al. | 528/28 |
| 4,891,166 A | 1/1990 | Schaefer et al. | 260/404.5 |
| 4,908,140 A | 3/1990 | Bausch et al. | 252/8.6 |
| 4,978,462 A | 12/1990 | Sheppard | 252/8.6 |
| 5,098,979 A | 3/1992 | O'Lenick, Jr. | 528/25 |
| 5,153,294 A | 10/1992 | O'Lenick, Jr. | 528/26 |
| 5,166,297 A | 11/1992 | O'Lenick, Jr. | 528/26 |
| 5,591,880 A | 1/1997 | O'Lenick, Jr. | 556/413 |
| 5,602,224 A | 2/1997 | Vrckovnik et al. | 528/21 |
| 5,650,529 A | 7/1997 | O'Lenick, Jr. | 556/418 |
| 5,807,956 A | 9/1998 | Czech | 528/28 |
| 5,969,077 A | 10/1999 | Schröck et al. | 528/31 |
| 5,981,681 A | 11/1999 | Czech | 528/27 |
| 6,177,511 B1 | 1/2001 | Dauth et al. | 524/838 |
| 6,211,139 B1 | 4/2001 | Keys et al. | 510/504 |
| 6,240,929 B1 | 6/2001 | Richard et al. | 132/202 |
| 6,242,554 B1 | 6/2001 | Busch et al. | 528/28 |
| 2004/0048996 A1 | 3/2004 | Lange et al. | 528/10 |
| 2004/0138400 A1 | 7/2004 | Lange et al. | 528/38 |

FOREIGN PATENT DOCUMENTS

| | | |
|---|---|---|
| DE | 3 236 466 | 5/1983 |
| DE | 3 719 086 | 10/1988 |
| DE | 43 18 536 | 12/1994 |
| DE | 198 03 468 | 8/1999 |
| EP | 0282720 | 9/1988 |
| EP | 0291871 | 11/1988 |
| EP | 441530 | 8/1991 |
| WO | WO 9914300 | 3/1999 |
| WO | WO 99/50338 | * 10/1999 |
| WO | WO 0071806 | 11/2000 |
| WO | WO 0071807 | 11/2000 |
| WO | WO 0127232 | 4/2001 |
| WO | WO 02 10257 | 2/2002 |
| WO | WO 0210256 | 2/2002 |
| WO | WO 0210259 | 2/2002 |

OTHER PUBLICATIONS

J. V. Gruber et al., Colloids and Surfaces B; Biointerfaces 19 (2000), 127-135.
W. Noll, Chemie und Technologie der Silicone, [=Chemistry and Technology of Silicones], VCH, Weinheim, 1968.
B. Marciniec, Comprehensive Handbook on Hydrosilylation, Pergamon Press, Oxford 1992, p. 122-124.
Organikum, Organisch-chemisches Grundparktikum [=Organikum, Basic Practice of Organic Chemistry], 17th edition, VEB Deutscher Verlag der Wissenschaften, Berlin, 1988, pp. 402-408.
Organikum, Organisch-chemisches Grundpraktikum [=Organikum, Basic Practice of Organic Chemistry], 17th edition, VEB Deutscher Verlag der Wissenschaften, Berlin, 1988, pp. 189-190.
Silicone, Chemie und Technologie [=Silicones, Chemistry and Technology], Vulkan-Verlag, Essen, 1989, pp. 5.
Organikum, Organisch-chemisches Grundpraktikum [=Organikum, Basic Practice of Organic Chemistry], 17th edition, VEB Deutscher Verlag der Wissenschaften, Berlin, 1988, pp. 196-199.
Silicone, Chemie und Technologie [=Silicones, Chemistry and Technology], Vulkan-Verlag, Essen 1989, pp. 82-84.
B. Marciniec, Comprehensive Handbook on Hydrosilylation, Pergamon Press, Oxford, 1992, pp. 116-121.
B. Marciniec, Comprehensive Handbook on Hydrosilylation, Pergamon Press, Oxford, 1992, pp. 127-130.
B. Marciniec, Comprehensive Handbook on Hydrosilylation, Pergamon Press, Oxford, 1992, pp. 134-137.
B. Marciniec, Comprehensive Handbook on Hydrosilylation, Pergamon Press, Oxford, 1992, pp. 151-155.

* cited by examiner

*Primary Examiner*—Marc S. Zimmer
(74) *Attorney, Agent, or Firm*—Norris McLaughlin & Marcus PA

(57) ABSTRACT

Hydrophilic polyquaternary polyorganosiloxane copolymers and their use as wash-resistant hydrophilic softeners.

18 Claims, No Drawings

BRANCHED POLYORGANOSILOXANE POLYMERS

This is a 371 of PCT/EP03/02861 filed 19 Mar. 2003 (international filing date).

The present invention relates to branched polyorganosiloxane polymers, a process for their production, their use, and compositions containing them. The invention relates in particular to hydrophilic polyquaternary polyorganosiloxane copolymers and their use in particular as wash-resistant hydrophilic softeners.

BACKGROUND OF THE INVENTION

Polysiloxanes containing amino groups are known as textile softeners (EP 441530). The introduction of amino structures modified by ethylene oxide/propylene oxide units as side chains causes an improvement of the effect (U.S. Pat. No. 5,591,880, U.S. Pat. No. 5,650,529). The alkylene oxide units permit in this case the selective setting of the hydrophilic-hydrophobic balance. Disadvantageous from the synthetic standpoint is the fact that, included in the synthesis strategy, there is the difficult esterification of amino alcohols with siloxane-bound carboxylic acid groups and, with respect to the softening properties, the general comb structure of the products.

To eliminate these disadvantage is has been proposed to convert α,ω-epoxymodified siloxanes with α,ω-aminofunctionalized alkylene oxides and to use these products as hydrophilic softeners (U.S. Pat. No. 5,807,956, U.S. Pat. No. 5,981,681).

To improve the substantivity, experiments were undertaken to introduce quaternary ammonium groups in alkylene oxide-modified siloxanes.

Branched alkylene oxide-modified polysiloxane quats have been synthesized from α,ω-OH terminated polysiloxanes and trialkoxysilanes by condensation. The quaternary ammonium structure is introduced via the silane, where the quaternary nitrogen atom is substituted with alkylene oxide units (U.S. Pat. No. 5,602,224).

Severe comb-like alkylene oxide-modified polysiloxane quats have also been described (U.S. Pat. No. 5,098,979). The hydroxyl groups of comb-like substituted polyether siloxanes are converted with epichlorohydrine into the corresponding chlorohydrine derivatives. Subsequently a quaternization is done with tertiary amines.

For this reason, the hydroxyl groups of comb-like substituted polyether siloxanes have been esterified alternatively with chloroacetic acid. Through the carbonyl activation the concluding quaternization can be completed in a simplified manner (U.S. Pat. No. 5,153,294, U.S. Pat. No. 5,166,297).

In U.S. Pat. No. 6,242,554 the α,ω-difunctional siloxane derivatives are described that each have a separate quaternary ammonium and alkylene oxide unit. These materials are distinguished by an improved compatibility with polar environments.

The reaction of α,ω-diepoxides with tertiary amines in the presence of acids provides α,ω-diquaternary siloxanes which can be used for the purposes of hair-grooming (DE-PS 3 719 086). Along with tetraalkyl-substituted quaternary ammonium structures, aromatic imidazolinium derivatives are also claimed.

A reduction of the ability to be washed out of the hair can be achieved if the α,ω-diepoxides are converted with ditertiary amines in the presence of acids into long-chain polyquaternary polysiloxanes (EP 282720).

Aromatic quaternary ammonium structures are not disclosed. Derivatives of this type are treated in U.S. Pat. No. 6,240,929. In a first step two diamines having two imidazole units are synthesized from imidazole and suitable difunctional alkylation agents, said diamines subsequently being converted into polyquaternary polysiloxanes in a manner analogous to EP 282720. Cationic compounds produced in this way should have a further increased compatibility with respect to the anionic surfactants present in cosmetic formulations. However, the resistance to being washed out of the hair relates to short-term attack of primarily water and very mild surfactants not irritating the skin while wash-resistant, hydrophilic softeners for textiles have to withstand the attack of concentrated surfactant solutions with high fat-dissolving and dirt-dissolving power. Making it more difficult in addition is the fact that modern detergents contain strongly alkaline complex promoters, oxidatively acting bleaches, and complex enzyme systems, with the fibers often being exposed to the action for hours at elevated temperatures.

Alternative approaches to the improvement of the compatibility with anionic surfactant systems or the efficiency of the siloxane deposition on surfaces are targeted at the use of greater amounts of cationic surfactants (WO 00-71806 and WO 00-71807) or the utilization of cationic polysaccharide derivatives (J. V. Gruber et al., Colloids and Surfaces B; Biointerfaces 19 (2000), 127-135) in mixtures with polydimethyl siloxanes.

Highly charged, very hydrophilic synthetic polycationics are also in the position to improve the compatibility with anionic surfactant systems (U.S. Pat. No. 6,211,139) or in the presence of solutions of anionic surfactants to associate with fibers (WO 99-14300). In the latter document, polyimidazolinium derivatives, among others, are described.

None of the proposals treated represents a satisfactory solution to the problem of obtaining the soft feel possible through silicone and the pronounced hydrophily after initial finishing of a textile material even when it is exposed to attack of aggressive detergent formulations, that is, among others, detergent formulations with a high pH value (>10) and highly active surfactants in the course of repeated washing processes at, in given cases, an elevated temperature.

A fundamentally different approach is described in DE-OS 3 236 466. The conversion of OH-terminated siloxanes with alkoxysilanes containing quaternary ammonium structures provides reactive intermediate products which are supposed to be cross-linked with suitable cross-linking agents, such as trialkoxysilanes, on the fiber surface to form wash-resistant layers. A decisive disadvantage of this approach is the fact that the necessary hours-long stability of an aqueous finishing bath cannot be guaranteed and unforeseen cross-linking reactions in the batch can already occur before the textile finishing.

Self-cross-linking emulsions of aminosiloxanes are also known (U.S. Pat. No. 4,661,577). For this, trialkoxysilyl structures terminal in the molecule are introduced.

A cross-linking of aminosiloxanes can also be achieved by reaction with epichlorohydrine or diepoxides (WO 01-27232) or, analogous to Michael addition, by a reaction with diacrylates (DE 198 03 468).

Alternative approaches with the participation of cross-linked structures deal with, among other things, mixtures of hydrocarbon-based quats (compounds containing quaternary ammonium groups) and cross-linked siloxanes (U.S. Pat. No. 4,908,140) or the additional incorporation of straight-chain siloxanes (U.S. Pat. No. 4,978,462).

WO 02-10257 describes linear polysiloxane compounds which contain polyalkylene oxide structural units, ammonium groups, and polysiloxane structural units in which the possibility of a branching is in fact mentioned but no branched polysiloxane compounds or actual branching components needed to build them are described. The mentioned multi-functional groups thus do not serve for building branches but rather the saturation within the linear main chain or for building monofunctional side chains.

These linear polysiloxane compounds, however, still always have disadvantages with regard to their substantivity.

Branched polysiloxane compounds were previously considered by those skilled in the art as unsuitable to serve as soluble or emulsifiable, i.e., applicable, softeners because they incline toward-the formation of highly molecular gels so that they cannot be applied to the fibers from aqueous solution.

It was thus completely surprising that the special, branched polysiloxane polymers, as they were prepared for the first time by the inventors of the present patent application, were, on the one hand, soluble and applicable and have, at the same time, a higher substantivity (durability), and even in many cases an increased softening action, with respect to the linear polysiloxane compounds.

The hydrophilic, polyquaternary polysiloxane copolymers according to the invention can thus lend textiles, after appropriate application, a soft feel typical of silicone and a pronounced hydrophilicity, and this profile of properties is also not lost after the action of detergent formulations during repeated washing processes at, in given cases, an elevated temperature.

Furthermore, the hydrophilic, polyquaternary polysiloxane copolymers according to the invention can serve as separate softeners or as softeners in formulations for washing fibers and textiles which are based on non-ionogenic or anionic/non-ionogenic surfactants as well as an aid to ironing and means for preventing or reversing creases in textiles.

SUMMARY OF THE INVENTION

The present invention thus provides branched polyorganosiloxane polymers containing at least one group of the structure

at least one group of the structure

at least one group of the structure

as well as at least one branching unit which is chosen from the group which consists of $S^v$ and $V^v$, where
  Groups V are connected to groups Q and S,
  Groups Q are not connected to groups S
  the groups S, $S^v$, V, $V^v$, and Q in a polymer molecule can be the same or different and where

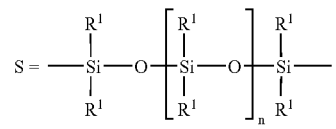

where
  $R^1$ can be the same or different and is chosen from the group which consists of: $C_1$ to $C_{22}$ alkyl, fluoro($C_1$-$C_{10}$) alkyl and $C_6$-$C_{10}$ aryl, n =0 to 1000
  $S^v$ is a three or higher valent organopolysiloxane unit,
  Q is a divalent organic group containing at least one ammonium group,
  V represents a divalent, straight-chain, cyclic or branched, saturated, unsaturated, or aromatic hydrocarbon group with up to 1,000 carbon atoms which, in given cases, can contain one or more groups
    chosen from chosen from —O—, —NH—, —NR$^1$—, where $R^1$ is defined as above,

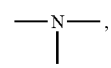

—C(O)—, and —C(S)—, and which, in given cases, can be substituted with one or more hydroxyl groups, $V^v$ represents a trivalent or higher valent, straight-chain, cyclic or branched, saturated, unsaturated, or aromatic hydrocarbon group with up to 1,000 carbon atoms which, in given cases, can contain one or more groups chosen from —O—, —NH—, —NR$^1$—, wherein $R^1$ is defined as above,

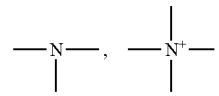

—C(O)—, and —C(S)—, and which, in given cases, can be substituted with one or more hydroxyl groups, and where the positive charges resulting from the ammonium group are neutralized by organic or inorganic acid anions and their acid addition salts.

DETAILED DESCRIPTION

In a preferred form of embodiment the divalent organic group Q containing at least one ammonium group is chosen from the group which consists of

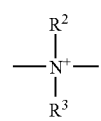

a quaternized imidazole unit of the structure

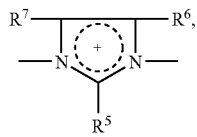

a quaternized pyrazole unit of the structure

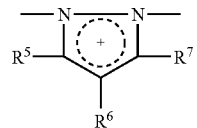

where $R^5$, $R^6$, and $R^7$ can be the same of different and are chosen from the group which consists of: H, halogen, hydroxyl group, nitro group, cyano group, thiol group, carboxyl group, alkyl group, monohydroxyalkyl group, polyhydroxylalkyl group, thioalkyl group, cyanoalkyl group, alkoxy group, acyl group, acetyloxy group, cycloalkyl group, aryl group, alkylaryl group, and groups of the type —$NHR^w$ in which $R^w$ means H, alkyl group, monohydroxyalkyl group, polyhydroxyalkyl group, acetyl group, ureido group, and the groups $R^6$ and $R^7$ with the carbon atoms binding them to the imidazole ring, or two of the groups $R^5$, $R^6$, and $R^7$ with the carbon atoms binding them to the pyrazole ring, can form aromatic five-element to seven-element rings, more preferably $R^5$, $R^6$, and $R^7$ are the same or different and are chosen from the group which consists of: H and $C_1$-$C_6$ alkyl, and the groups $R^6$ and $R^7$ with the carbon atoms binding them to the imidazole ring, or two of the groups $R^5$, $R^6$, and $R^7$ with the carbon atoms binding them to the pyrazole ring, can form a phenyl ring.

a diquaternized piperazine unit of the structure

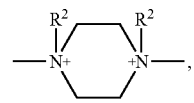

a monoquaternized piperazine unit of the structure

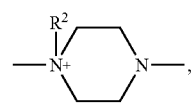

a monoquaternized piperazine unit of the structure

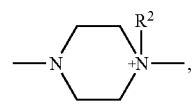

a diquaternized unit of the structure

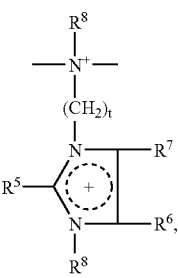

a monoquaternized unit of the structure

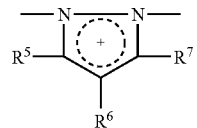

a monoquaternized unit of the structure

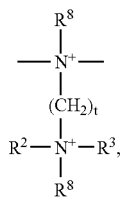

a diquaternized unit of the structure a monoquaternized unit of the structure

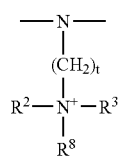

a monoquaternized unit of the structure

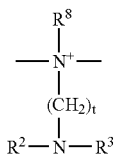

where t=2 to 10 and $R^2$=H or represents a monovalent, straight-chain, cyclic or branched, saturated, unsaturated, or aromatic hydrocarbon group with up to 40 carbon atoms which can contain one or more groups chosen from —O—, —NH—, —C(O)—, and —C(S)—, and which, in given cases, can be substituted with one or more hydroxyl groups, $R^2$ preferably represents a monovalent or divalent, straight-chain, cyclic or branched, saturated, unsaturated, or aromatic hydrocarbon group with up to 30 carbon atoms (for non-aromatic hydrocarbon groups with 1 to 30 carbon atoms) which can contain one or more groups chosen from —O—, —NH—, —C(O)—, and —C(S)—, and which, in given cases, can be substituted with one or more hydroxyl groups, Still more preferably $R^2$=

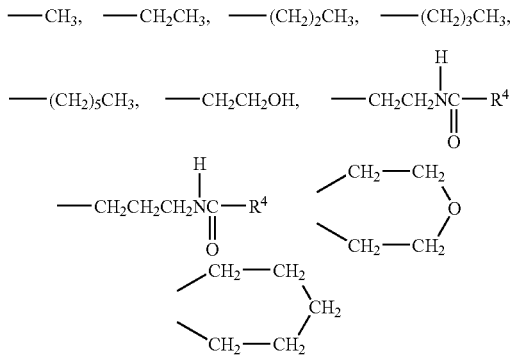

with $R^4$=a straight-chain, cyclic or branched $C_1$ to $C_{18}$ hydrocarbon group which can contain one or more groups chosen from —O—, —NH—, —C(O)—, and —C(S)—, and which can be substituted with one or more hydroxyl groups, especially unsubstituted $C_5$ to $C_{17}$ hydrocarbon groups which are derived from the corresponding fatty acids or hydroxylated $C_3$ to $C_{17}$ groups which can be traced back to hydroxylated carboxylic acids, especially saccharide carboxylic acids, and quite especially mean

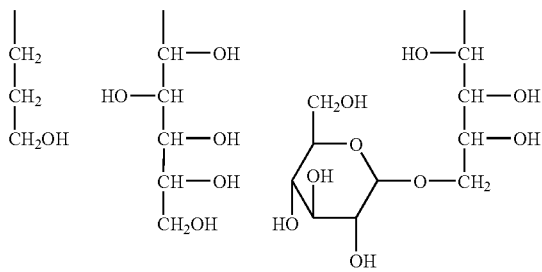

$R^3$ can have the meaning of $R^2$, where $R^2$ and $R^3$ can be the same or different or $R^2$ and $R^3$ together with the positively charged nitrogen atom form a five- to seven-element heterocycle which, in given cases, can have in addition one or more nitrogen, oxygen, and/or sulfur atoms, $R^8$ has the meaning of $R^2$, where $R^8$ and $R^2$ can be the same or different.

In an additional preferred form of embodiment of the branched polyorganosiloxane polymers according to the invention S is a group of the structure:

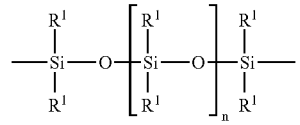

wherein $R^1$ is chosen from the group which consists of methyl, ethyl, trifluoropropyl, and phenyl and n is from 0 to 500, more preferably 0 to 350, particularly preferably 0 to 160 and 160 to 350, quite particularly preferably 0 to 110 and 200 to 350, specifically preferably 0 to 80, quite specifically preferably 0 to 50.

In an additional preferred form of embodiment of the branched polyorganosiloxane polymers according to the invention V represents a divalent, straight-chain, cyclic or branched, saturated, unsaturated, or aromatic hydrocarbon group with up to 400 carbon atoms which can contain one or more groups chosen from —O—, —NH—, —$NR^1$—, where $R^1$ is defined as above,

—C(O)—, and —C(S)—, and can be substituted with one or more hydroxyl groups.

The combination of groups

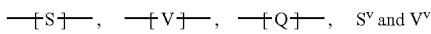

is done in the branched polyorganosiloxane polymers according to the invention so that the groups V (V and $V^v$) are connected to the groups Q or S(S and $S^v$) but the groups Q are not connected to the groups (S and $S^v$). Moreover, all the combinations of said groups are possible where, according to production, block-like and/or static copolymers can result.

Thus, for example, block-like sequences of -(S-V) units or -(Q-V) units can be present. In a preferred form of embodiment of the branched polyorganosiloxane polymers according to the invention they contain repeating units of the structure

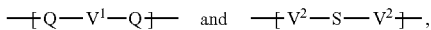

where Q and S are defined as above, $V^1$ and $V^2$ have the meaning of V but are different from one another along with said branching units ($S^v$, $V^{1v}$ or $V^{2v}$). Preferably, the branched polyorganosiloxane polymers according to the invention have repeating units of the structure

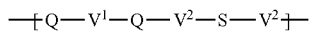

where Q, $V^1$, $V^2$, and S are defined as above along with said branching units.

In an additional preferred form of embodiment of the branched polyorganosiloxane polymers according to the invention they contain repeating units of the structure

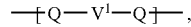

where Q is defined as above, and —$V^1$— is chosen from groups of the structures:
- —$R^9$— where $R^9$ represents a divalent, saturated or simply or multiply unsaturated, straight-chain or branched, hydrocarbon group with two to 25 carbon atoms such as
- —$(CH_2)_u C(O)O$—$[(CH_2CH_2O)_q$—$(CH_2CH(CH_3)O)_r]$—$C(O)(CH_2)_u$—
- —$(CH_2)_u C(O)O$—$R^9$—O—$C(O)(CH_2)_u$—, where $R^9$ is defined as previously,
- —$(CH_2)_u$—$R^{10}$—$(CH_2)_u$—, where $R^{10}$ is an aromatic group,
- —$[CH_2CH_2O]_q[CH_2CH(CH_3)O]_r$—$CH_2CH_2$—,
- —$CH(CH_3)CH_2O[CH_2CH_2O]_q[CH_2CH(CH_3)O]_r$ $CH_2CH(CH_3)$)
- —$CH_2CH(OH)CH_2$—,
- —$CH_2CH(OH)(CH_2)_2CH(OH)CH_2$—,
- —$CH_2CH(OH)CH_2OCH_2CH(OH)CH_2OCH_2CH(OH)$ $CH_2$— and
- $CH_2CH(OH)CH_2O$—$[CH_2CH_2O]_q$—$[CH_2CH(CH_3)O]_r$ $CH_2CH(OH)CH_2$— where
u is from 1 to 3,
q and r are from 0 to 200, preferably from 0 to 100, more preferably from 0 to 70, and particularly
preferably 0 to 40, and
q+r>0.
Preferred variants of $V^1$ are structures of the formula

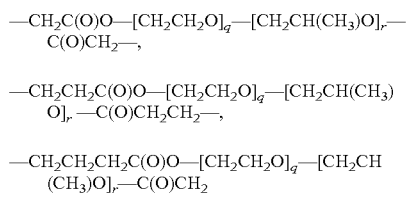

esterified alkylene, alkenylene, alkinylene units, especially of the formulas

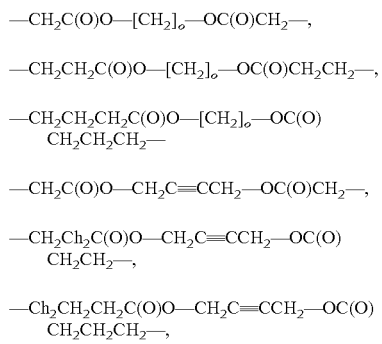

—$CH_2C(O)O$—$Ch_2CH=CHCH_2$—$OC(O)CH_2$—,

—$CH_2CH_2C(O)O$—$CH_2CH=CHCH_2$—$OC(O)$ $CH_2CH_2$—,

—$CH_2CH_2CH_2C(O)O$—$CH_2CH=CHCH_2$—$OC(O)$ $CH_2CH_2CH_2$—, alkylene, alkenylene, alkinylene, and aryl units, especially of the structure —$[CH_2]_o$— with o=2 to 6

—$CH_2C\equiv CCH_2$—, —$CH_2CH=CHCH_2$—, —CH $(CH_3)CH_2CH_2$—,

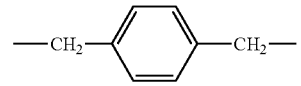

polyalkylene oxide units, especially of the formulas

—$[CH_2CH_2O]_q$—$[CH_2CH(CH_3)O]_r$—$CH_2CH_2$—,

—$CH(CH_3)CH_2O[CH_2CH_2O]_q$—$[CH_2CH(CH_3)O]_r$ —$CH_2CH(CH_3)$— with monohydroxyfunctional units, dihydroxyfunctional units, or polyhydroxyfunctional units, especially of the formulas

—$CH_2CH(OH)CH_2$—, —$CH_2CH(OH)(CH_2)_2CH$ $(OH)CH_2$—,

—$CH_2CH(OH)CH_2OCH_2CH(OH)CH_2OCH_2CH(OH)$ $CH_2$—,

—$CH_2CH(OH)CH_2O$—$[CH_2CH_2O]_q$—$[CH_2CH$ $(CH_3)O]_r$—$CH_2CH(OH)CH_2$— with q=0 to 200 r=0 to 200

Preferably q=1 to 50, in particular 2 to 50, especially 1 to 20, quite especially 1 to 10, as well as 1 or 2, r=0 to 100, in particular 0 to 50, especially 0 to 20, quite especially 0 to 10, as well as 0 or 1 or 2.

In an additional preferred form of embodiment of the branched polyorganosiloxane polymers according to the invention they contain repeating units of the structure

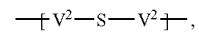

where invention $V^2$ is a divalent, straight-chain, cyclic or branched, saturated, unsaturated, or aromatic $C_2$ to $C_{16}$ hydrocarbon group which can contain one or more groups chosen from —O—, —NH—, —$NR^1$—, where $R^1$ is defined as above,

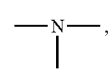

—C(O)—, and —C(S)—, and can be substituted with one or more hydroxyl groups. Still more preferably —$V^2$— is chosen from groups of the structures:

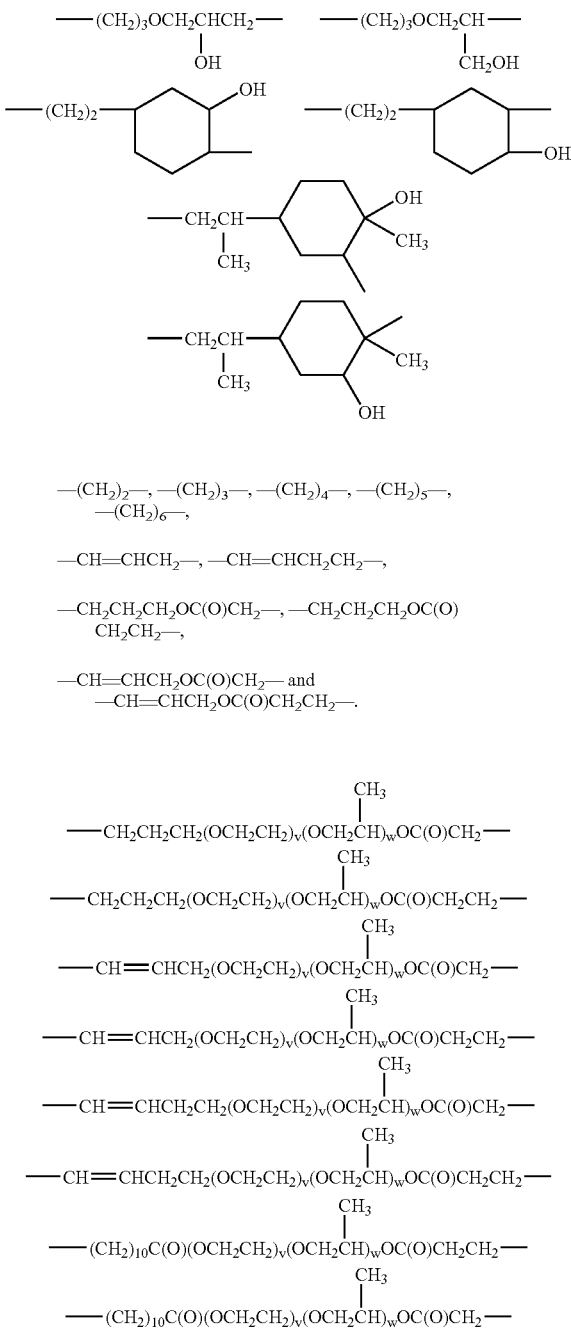

with v+w≧0.

In a preferred form of embodiment of the invention, the branched polyorganosiloxane polymer has a branching unit $S^v$ which is a trivalent or higher valent organopolysiloxane group which has at least three silicon atoms which are each connected to three or more groups V or $V^v$ via a bond to a carbon atom of the respective group V or $V^v$.

The group $S^v$ has, in addition to the group S, more of the following siloxy units which make it possible to link 3 and more bonds to $V^2$ or $V^{2v}$. $S^v$ includes: equilibration and condensation products, the following methylsiloxane units contain: M, D, T, and Q (W. Noll, Chemie und Technologie der Silicone, [=Chemistry and Technology of Silicones], VCH, Weinheim, 1968) as well as units M', D', and T' which are derived from M-, D-, and T-units in which formally by omission of a methyl group a free valence is formed which bonds to V.

Examples of the $S^v$ groups include, for example, at least trivalent organopolysiloxane groups of the structure:

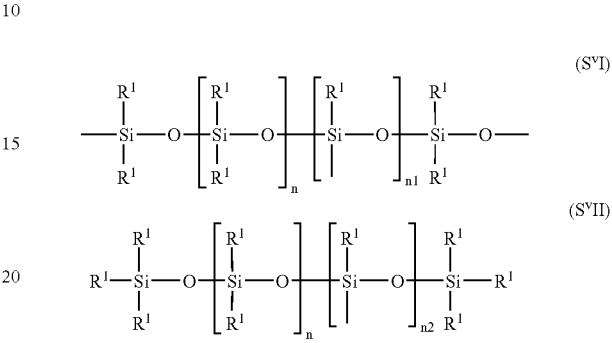

with $n^1 ≧ 1$ ($S^vI$) for ($S^vI$): with $n^2 ≧ 3$

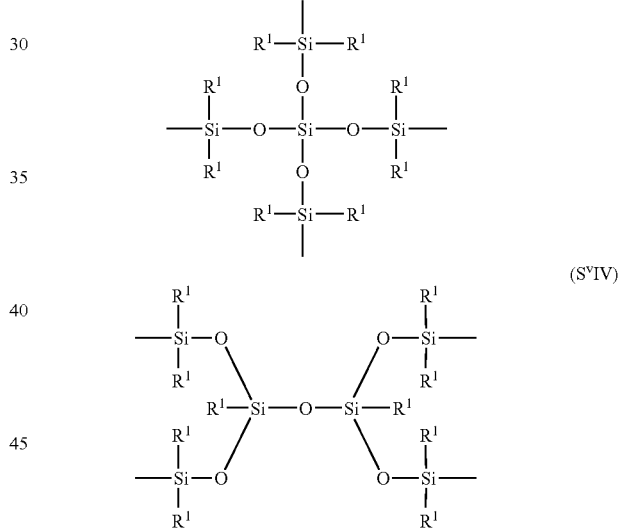

The molar percentage of the bonds in $S^v$ to $V^2$ or $V^2$, is 0.002 to 50%, preferably 0.01 to 30%, especially preferably 0.1 to 20%.

In an additional preferred form of embodiment of the invention, the branched polyorganosiloxane polymers have a branching group of the formula

where $V^{1v}(-Q-)_x$ is a trivalent or higher valent group, Q is defined as above, and x is a whole number of at least three, and where $V^{1v}$ is chosen from the group which consists of:

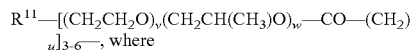

$R^{11}$ is a trivalent or hexavalent group which is derived from a polyol in which 3 to 6 hydroxyl-hydrogen atoms are substituted, v and w are from 0 to 200,
v+w≧0, and
u=1 to 3

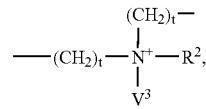

R¹¹, v, and w are defined as above

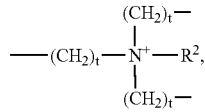

where t is from 2 to 10 and $R^2$ is defined as above, preferably H or methyl,

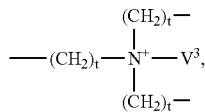

where t is from 2 to 10 and $V^3$ is a partial structure which is derived from V or $V^v$, and, $$-(CH_2)_t-N^+-R^2,$$
with $(CH_2)_t-$ and $V^3$ substituents where t is from 2 to 10 and $R^2$ and $V^3$ are defined as above, $R^2$ is preferably H or methyl.

The aforementioned polyol is preferably chosen from the group which consists of: glycerol, trimethylolpropane, pentaerythritol, sorbitol, and sorbitan. Examples for $V^{1v}$ include: trivalent and higher valent structures of based on esters of polyols with $C_2$ to $C_6$ carboxylic acid groups or ethers of beta-hydroxyalkyl groups, proceeding from the conversion of polyols with oxirans, such as epichlorohydrine, vinylcyclohexene monoepoxide, vinylcyclohexene diepoxide.

Along with this, various ones of these groups can form the group $V^{1v}$ on the polyol.

Preferred polyols are glycerol, trimethylolpropane, pentaerythritol, sorbitol, and sorbitan, which can be esterified with chloroacetic acid or chloropropionic acid.

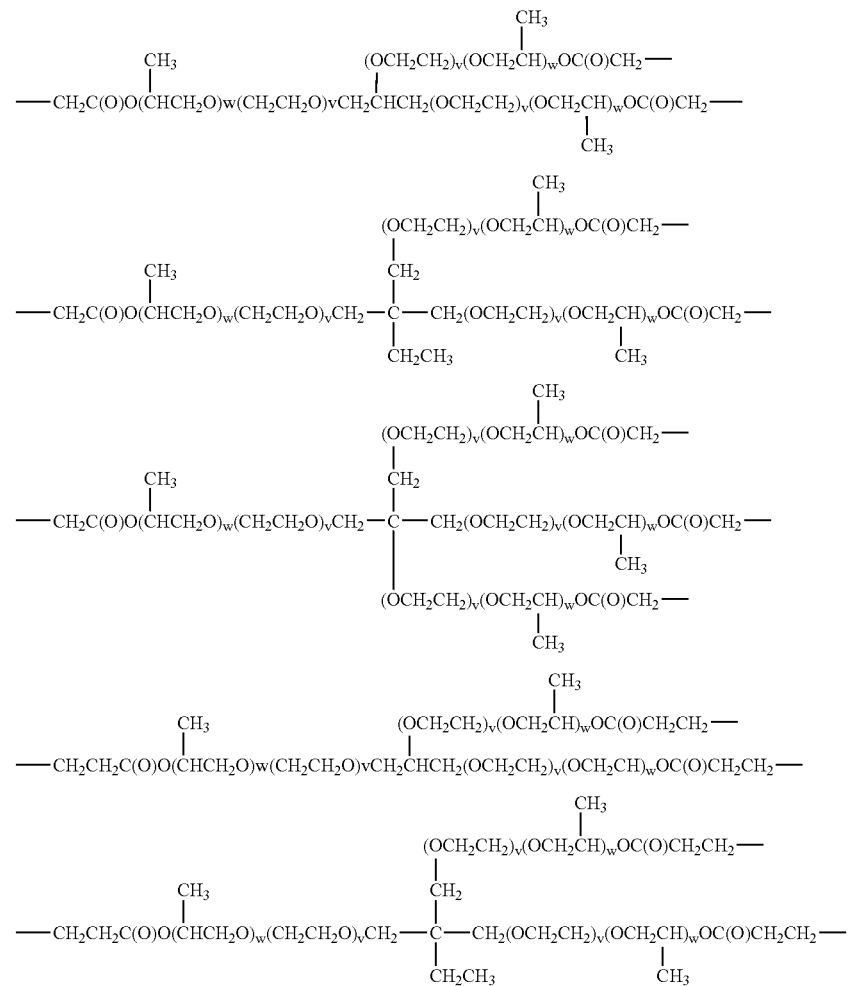

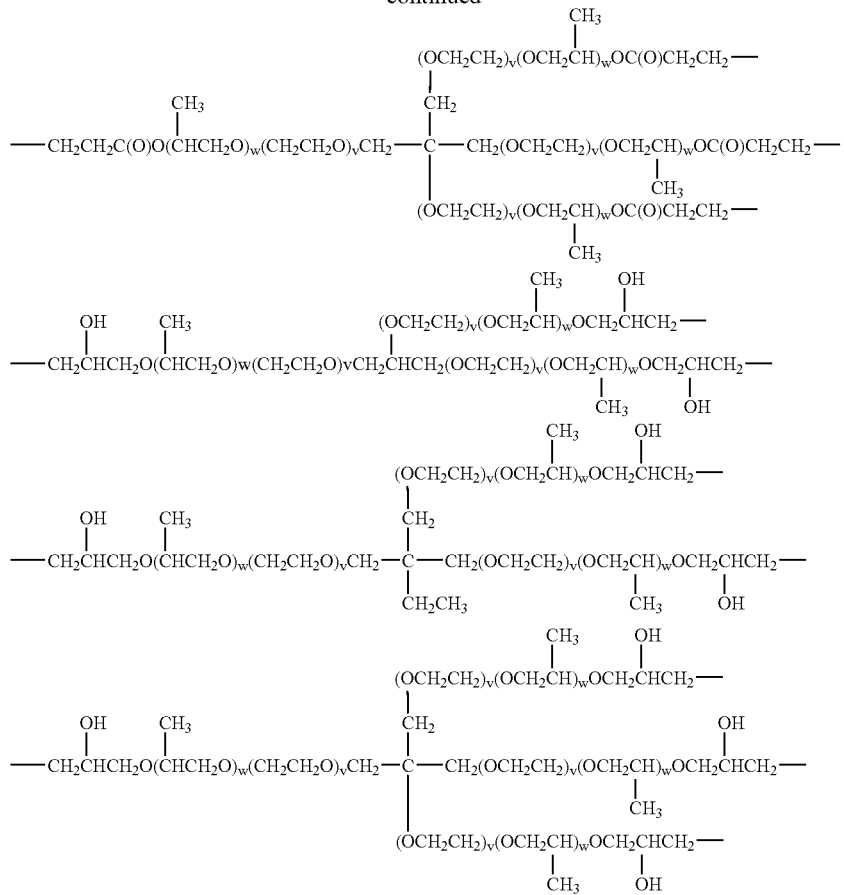

with v+w≧0

The molar percentage of $V^{1v}$ in $V^1$ is 0.002 to 50%, preferably 0.01 to 30%, especially preferably 0.1 to 20%.

In addition, a part of the Q groups binds to $V^{2v}$. These are, for example, trivalent and higher valent structures of $V^{2v}$, based on esters of polyols with $C_2$ to $C_6$ carboxylic acid groups or ethers of beta-hydroxyalkyl groups, proceeding from the conversion of polyols with oxirans, such as epichlorohydrine, vinylcyclohexene monoepoxide, vinylcyclohexene diepoxide.

Along with this, various ones of these groups can form on the polyol, together with it, the group $V^{2v}$. In analogy thereto, the group $S^v$ can be linked to different groups $V^2$ or $V^{2v}$.

The units $V^2$ and $S^v$ are defined as above under $V^2$ and can be linked to $S^v$ in this form of embodiment in such a manner that different $V^2$ groups bind to an $S^v$. Likewise, different groups $V^{2v}$ and a group $S^v$ can be bound.

In an additional form of embodiment of the invention, the branched polyorganosiloxane polymers $S^v$ can be bound to a branching group of the structure $V^{2v}$ which is connected to at least one group S or $S^v$ and where $V^2$ is a trivalent or higher valent group which is chosen from the group which consists of:

$-(Z-)_y R^{12}[-(CH_2CH_2O)_v(CH_2CH(CH_3)O)_w-CO-(CH_2)_u]_z-$, where $R^{12}$ is a trivalent or hexavalent group which is derived from a polyol in which 3 to 6 hydroxyl-hydrogen atoms are substituted, and Z is a divalent hydrocarbon group with up to 20 carbon atoms which can contain one or more groups chosen from —O— and —C(O)—, and which, in given cases, can be substituted with one or more hydroxyl groups, and where the group Z is bonded by one of its carbon atoms to a silicon atom of the groups S or $S^v$, v and w are from 0 to 200, v+w≧0, u=1 to 3, y=1 to 6, preferably 1, z=0 to 5, preferably 2 to 5, and z+y=3 to 6, preferably 3,

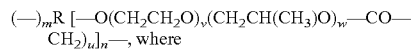

$R^{13}$ is a trivalent or hexavalent, saturated or unsaturated, linear, branched or cyclic hydrocarbon group with up to 10 carbon atoms, (—) represents a single bond to a silicon atom of the group S or $S^v$, v and w are from 0 to 200, v+w≧0, u=1 to 3, m 1 or 2, preferably 1, n=1 to 5, preferably 2 to 5, and m+n=3 to 6, preferably 3,

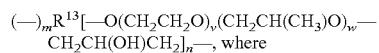

m, $R^{13}$, v, w, and n are defined as above,

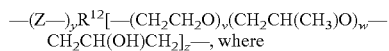

Z, y, $R^{12}$, v, w, and z are defined as above.

Examples of the groups $V^{2v}$ include:

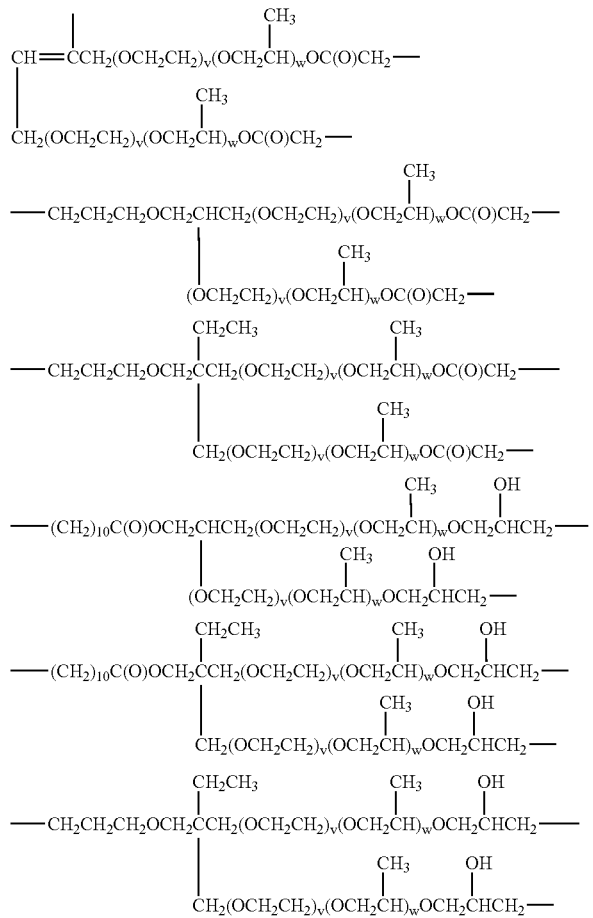
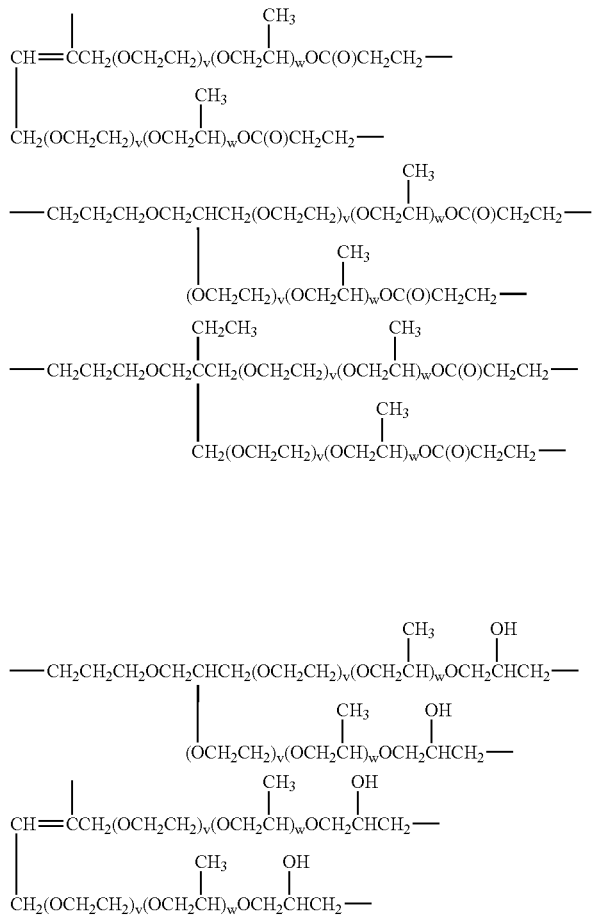

with v+w≧0.

The molar percentage of $V^{2v}$ in $V^2$ is 0.002 to 50%, preferably 0.01 to 30%, especially preferably 0.1 to 20%.

In a preferred form of embodiment of the branched polyorganosiloxane polymers, the molar ratio of the sum of the branching units $S^v$ and $V^v$ to the sum of the linear repeating units S, V, and Q is 0.001 to 20%.

In an additional preferred form of embodiment, the branched polyorganosiloxane polymers contain the branching units $V^v$ and $S^v$, where the molar ratio of $V^v$ to V is preferably from 0.002% to 20% and the molar ratio of $S^v$ to S is preferably from 0.002 to 20%.

In order to avoid the formation of gel-like branched polyorganosiloxane polymers which are not completely soluble, the amount of the branching units is, in accordance with this aim, limited from above.

An additional limiting of the molecular weight is caused by the final shortstopping arising in the reaction between epoxides and water or alcohol, or alternatively by the additional use of trialkylamines.

That means the branched polyorganosiloxane polymers can also have, along with the terminal groups resulting naturally from the conversion of the monomeric starting materials, monofunctional chain termination agents such as trialkylamines, etc., and, for example, ammonium, ether, or hydroxy-terminal groups resulting therefrom. Moreover, the molecular weight can be limited via the selection and stochiometry of the units S, V, and Q.

The branched polyorganosiloxane polymers according to the invention furthermore contain organic or inorganic acid anions for the neutralization of the positive charges resulting from the ammonium groups. Moreover, amino groups present can be converted by the addition of inorganic or organic acids into the corresponding acid addition salts which also are a part of the object of the invention. Organic or inorganic acid groups are groups which result formally from the elimination of one or more protons from organic or inorganic acids and include, for example, halide ions, especially chloride and bromide, alkylsulfates, especially methosulfate, carboxylates, especially acetate, propionate, octanoate, decanoate, dodecanoate, tetradecanoate, hexadecanoate, octadecanoate, oleate, sulfonates, especially toluene sulfonate. However, other anions can also be introduced by ion exchange. To be named are, for example, organic anions such as polyether carboxylates and polyether sulfates. Preferred are, for example, salts of fatty acids and chloride. The organic or inorganic anionic acid groups can be the same or different from one another in the branched polyorganosiloxane polymers according to the invention.

The invention relates furthermore to a process for the production of the branched polyorganosiloxane polymers which includes the conversion of:

a) at least one organic compound which has two amino groups and which can contain a polyorganosiloxane group, with
b) at least one organic compound which has two epoxy groups and which can contain a polyorganosiloxane group, with
c) at least one organic compound which has two halogen alkylcarbonyloxy groups and which can contain a polyorganosiloxane group, as well as
d) at least one branching compound which is derived from one of the organic compounds a), b), and/or c) in such a manner that they each have at least one additional amine, epoxy, or chloroalkylcarbonyloxy functionality with the specification that at least one of the compounds a) to d) contains a polyorganosiloxane group.

The starting point for the syntheses of the substances according to the invention are $\alpha,\omega$-Si—H functionalized siloxanes of the general structure

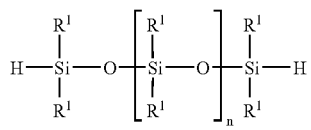

where $R^1$ and n have the meanings specified above. To the extent that they are not available commercially, these siloxanes can be produced according to known processes, for example, by acidic equilibration or condensation (Silicone, Chemie und Technologie [=Silicones, Chemistry and Technology], Vulkan-Verlag, Essen 1989, pp. 82-84).

The hydrogen siloxanes can be converted to the structural elements S—$V^2$ and S—$V^2$—Q, for example, on two paths.

On the one hand, it is possible first to bond unsaturated structures bearing tertiary amino functions, e.g. N,N-dimethylallylamine, by hydrosilylation directly to the hydrogen siloxane in $\alpha,\omega$-position. This process is generally known (B. Marciniec, Comprehensive Handbook on Hydrosilylation, Pergamon Press, Oxford 1992, P. 122-124).

On the other hand it is preferred to first generate by hydrosilylation reactive $\alpha,\omega$-functionalized intermediate products which subsequently can be converted into $\alpha,\omega$-ditertiary amino structures or directly into quaternary ammonium structures. Suitable starting substances for the generation of reactive intermediate stages are, for example, halogenated alkenes or alkines, especially allyl chloride, allyl bromide, chloropropine, and chlorobutine, unsaturated halogen carboxylic acid esters, especially chloroacetic acid allyl ester, chloroacetic acid propargyl ester, 3-chloropropionic acid allyl ester, and, 3-chloropropionic acid propargyl ester and epoxyfunctional alkenes, for example, vinylcyclohexene oxide and allylglycid ether. The general execution of hydrosilylations with representatives of said groups of substances is also known (B. Marciniec, Comprehensive Handbook on Hydrosilylation, Pergamon Press, Oxford, 1992, pp. 116-121, 127-130, 134-137, 151-155).

In a subsequent step, the reactive intermediate stages can then be brought into reaction with, for example, with compounds bearing primary, secondary, or tertiary amino functions. Suitable representatives are N,N-dialkylamines, for example, dimethylamine, diethylamine, dibutylamine, diethanolamine, and N-methylglucamine, cyclic secondary amines, for example, morpholine and peperidine, amino amides bearing secondary amino functions, for example, the conversion products of diethylene triamine or dipropylene triamine with lactones such as $\gamma$-butyrolactone, gluconic acid-$\delta$-lactone, and glucopyranosyl arabinonic acid lactone (DE-OS 43 18 536, Examples 11a, 12a, 13a) or secondary-tertiary diamines (amines with secondary and tertiary amine units) such as, for example, N-methylpiperazine. It is especially preferred to utilize corresponding imidazole or pyrazole derivatives, especially imidazole and pyrazole to introduce tertiary amino functions.

As partners for the epoxide derivatives preferably used in one form of embodiment as a possible reactive component, said secondary-tertiary diamines are particularly suitable, as are imidazole and pyrazole. In this manner, the alkylations can be directed regioselectively and without additional expenditure in nitrogen atoms bearing the hydrogen atoms.

To assure a quantitative conversion of the reactive groupings into tertiary amino structures the amines are used in a ratio of $1 \leq (\Sigma$ secondary amino groups:reactive groups$) \leq 10$, preferably 1 to 3, especially 1 to 2, particularly especially 1. An amine excess must, in given cases, be removed.

The binding of the above-described $\alpha,\omega$-ditertiary aminosiloxanes to a unit —$V^1$— leads to the formation of Q.

A preliminary preparation of a precondensate -Q-$V^1$-Q- terminated essentially by amino groups can, on the other hand, open the possibility of implementing the copolymer formation directly with suitable reactive intermediate stages, for example, epoxy derivatives.

It is also preferred to present together, and subsequently to bring to reaction, the reactive intermediate stages and the starting components for building the sequence -Q-$V^1$-Q-.

Finally, it is possible to dose the reactive intermediate stages in increments into the presented components for building the sequence -Q-$V^1$-Q- over a period of time, or, vice versa, to add these components in increments to the reactive intermediate stages.

Independent of the choice of one of the reaction paths described above and the question closely associated therewith whether amino units first limit the siloxane or the precondensate, a total stochiometry should be adhered to with regard to the molar amounts which can be described in essence by $\Sigma$ (primary+secondary+tertiary N):$\Sigma$(reactive groups on the siloxane+reactive groups on linkers forming $V^1$)=1:1.

In the scope of the invention, it is possible to deviate from this preferred total stochiometry. However, products are then obtained which leave an excess of a non-reacting starting component.

Along with the reaction's total stochiometry treated above, the choice of the precursors (n) forming the linkers $V^1$ is of great importance.

Suitable precursors (starting components) are, on the one hand, the halogen carboxylic acid esters of the alkylene oxides. Preferred starting materials for their synthesis' are low-molecular, oligomeric and polymeric alkylene oxides of the general composition

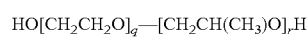

$$HO[CH_2CH_2O]_q\text{—}[CH_2CH(CH_3)O]_rH$$

where q and r have the meanings specified above. Preferred representatives with regard to the alkylene oxide block are ethylene glycol, diethylene glycol, triethylene glycol, tetraethylene glycol, the oligoethylene glycols with molecular weights of 300 to 1000 g/mol, especially 400, 600, and 800 as well as 1,2-propylene glycol, 1,3-propylene glycol, and dipropylene glycol.

The esterificiation of the alkylene oxides is done in a manner known per se (Organikum, Organisch-chemisches Grundpraktikum [=Organikum, Basic Practice of Organic Chemistry], 17th edition, VEB Deutscher Verlag der Wissenschaften, Berlin, 1988, pp. 402-408) by reaction with the $C_2$-halogen carboxylic acids to $C_4$-halogen carboxylic acids, their anhydrides, or acid chlorides. Preferably the acid chlorides of chloroacetic acid and 3-chloropropionic acid are used and the reaction carried out in the absence of solvents.

In an analogous manner alkane diols, alkene diols, and alkine diols can be converted into the corresponding reactive ester derivatives. Exemplary alcohols are 1,4-butandiol, 1,6-hexandiol, 1,4-but(2-)enol, and 1,4-but(2-)inol.

The introduction of alkylene, alkenylene, alkinylene, and aryl units is preferably done starting from the corresponding halides, especially chlorides and bromides. Exemplary representatives are 1,6-dichlorohexane, 1,4-dichlorobut(2-)ene, 1,4-dichlorobut(2-)ine, and 1,4-bis(chloromethyl)benzene.

Polyalkylene oxide units can also be introduced via the α,ω-dihalogen compounds. These are from the oligomeric and polymeric alkylene oxides of the general composition

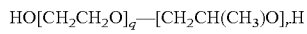

where q and r have the meanings specified above, accessible, for example, by chlorination of the hydroxyl groups with $SOCl_2$ (Organikum, Oganisch-chemisches Grundpraktikum [Organikum, Basic Practice of Organic Chemistry], 17th edition, VEB Deutscher Verlag der Wissenschaften, Berlin, 1988, pp. 189-190).

Monohydroxyfunctional units, dihydroxyfunctional units, or polyhydroxyfunctional units can be introduced as the linker $V^1$ starting from epoxide derivatives.

Commercial examples are 1-chloro-2,3-epoxypropane, glycerol-1,3-bis-glycidyl ether, and diethylene glycol diglycidyl ether, and neopentyl glycol diglycidyl ether.

To the extent that they are not available commercially, the desired diepoxides can, for example, be synthesized by reaction of the corresponding diols with 1-chloro-2,3-epoxypropane under alkaline conditions.

In the use of epoxides as starting materials for building $V^1$ it is to be noted that for alkylation of tertiary amino groups one mol $H^+$ per mole is to be added per mole epoxide/tertiary amine.

The choice of suitable amines as starting components for building Q also determines to a high degree the molecular structure. The use of ditertiary amines, e.g. N,N,N',N'-tetramethyl ethylene diamine, N,N,N',N'-tetramethyl tetraethylene diamine, N,N,N',N'-tetramethyl hexamethylene diamine, N,N'-dimethyl piperazine, leads to products in which each nitrogen atom of the repeating unit is quaternized.

The use of secondary-tertiary diamines, e.g. N-methylpiperazine, opens the way to repeating units -Q-$V^1$-Q- in which tertiary and quaternary amine or ammonium structures are present in the ratio 1:1. A partial or complete subsequent quaternization of remaining tertiary amino structure represents a preferred variant for the setting of a desired high density of the quaternary ammonium groups. The corresponding aromatic amines imidazole or pyrazole lead to products with a delocalized charge.

With the use of primary-tertiary diamines (amines with primary and tertiary amine units), for example N,N-dimethyl propylene diamine and 1-(3-aminopropyl)imidazole, especially in combination with diepoxides, comb-like structures can be built for which the degree of quaternization during a final alkylation is optional. In principle, degrees of quaternization of, on average, less than one quaternary ammonium group per repeating unit -Q-$V^1$-Q- are set. It is, however, preferred to quaternize at least one nitrogen atom per repeating unit Q-$V^1$-Q-.

Starting from the disecondary amines, e.g. piperazine, N,N'-bis(2-hydroxyethyl)-hexamethylene diamine, N,N'-bis(2-hydroxpropyl)-hexamethylene diamine, repeating units -Q-$V^1$-Q- can also be synthesized with an average content of less than one quaternary ammonium group. The disecondary amines provide in this case first polytertiary aminomodified siloxane copolymers which can be partially or completely quaternized in a subsequent reaction. It is, however, also preferred in this variant to quaternize at least one nitrogen atom per repeating unit.

Coming into consideration as suitable quaternization agents are the generally known groups of substances such as alkyl halides, halogen carboxylic acid ester, epoxide derivatives in the presence of $H^+$ and dialkylsulfates, especially dimethyl sulfate.

The production of disecondary amines not available commercially is done in a preferred form of embodiment starting from the corresponding primary amines, e.g. hexamethylene diamine, by alkylation with epoxides such as, for example, ethylene oxide, propylene oxide, or isopropylglycid ether utilizing the different reaction rates of primary and secondary amines.

Of decisive importance for the synthesis of the compounds according to the invention are the preparation and the use of cross-liking agents.

The introduction of $M^H$- in D-units to an α,ω-functionalized siloxane chain S is done just as that of branching T-units and Q-units into other D-units or D'-units or T'-units by acidic equilibration or condensation. It is known: (Silicone, Chemie und Technologie [=Silicones, Chemistry and Technology], Vulkan-Verlag, Essen, 1989, pp. 5, 82-84). By combining $M^H$-containing structures with D-containing structures, T-containing structures, or Q-containing structures, the desired terminal or lateral (D' or T') reactively functionalized groups $S^v$ can be obtained.

An equilibration in the presence of $D^H$-containing structures and, in given cases, $M^H$-containing structures provides, SiH-functionalized in a comb-like manner, products which, after appropriate reactive functionalization with, for example, unsaturated glycidyl or halogen carboxylic acid ester functions, can serve as cross-linking agents consisting of $S^v$—$(V^2)_{-\geq 3}$. The advantage of these siloxane-based $S^v$—$(V^2)_{-\geq 3}$— cross-linking agents is the great variability of the structure which can be adapted to the purpose of use. To be emphasized here are the possibilities, on the one hand by the use of alkoxylated cross-linking structures ($V^2$=polyether groups) to influence the hydrophily of the overall material, and, on the other hand, to increase the degree of branching by using, for example, butindiole structures.

Preferred reactive cross-linking agents in the sense of $S^v$ can be based on $M^H$-rich structures, for example, on $Q(M^H)_4$, $T(M^H)_3$, $(M^H)_2T-T(M^H)_2$ (EP 291871). Into this these siloxane-based starting materials are catalytically converted with olefinically or acetylenically unsaturated epoxides, e.g. allylglycid ether or halogen carboxylic acid esters, e.g. chloroacetic acid propinylester or the diester of ethylene glycol with undecene carboxylic acid and chloroacetic acid.

Hydrocarbon-based cross-linking agents in the sense of $V^{1v}$ are based, on the one hand, preferably on polyhydroxylated compounds, for example, such as glycerol, trimethylolpropane, pentaerythritol, or sorbitol. These can be esterified easily and in analogy to the already treated esterification of alkylene oxides with $C_2$-halogen carboxylic acids to $C_4$-halogen carboxylic acids, their acid chlorides, or their anhydrides (Organikum, Organisch-chemisches Grundpraktikum [=Organikum, Basic Practice of Organic Chemistry], 17th edition, VEB Deutscher Verlag der Wissenschaften, Berlin, 1988, pp. 402-408). Also in these cases it is possible, through a pre-positioned alkoxylation ($V^{1\nu}$=polyether groups) to increase the hydrophily of the cross linking agent. The halogen carboxylic acid esters synthesized in the described manner have due to the carbonyl activation of the halogen function a particularly high potential for the alkylation of tertiary amino groups.

On the other hand, glycidylfunctionalized cross-linking agents on the basis of hydrocarbon; are preferred for $V^{1\nu}$. These are either commercially available, such as, for example, triglycidyl derivatives (Aldrich) based on glycerol, or can also be produced by alkaline catalyzed addition of epichlorohydrine to the desired polyhydroxylated hydrocarbon. Preferred starting materials are the already mentioned glycerol, trimethylolpropane, pentaerythritol, or sorbitol. Also in this case a pre-positioned alkoxylation provides a more hydrophilic cross-linking agent.

The cross-linking agents used in the sense of $V^{1\nu}$ contain at least 3 reactive groups capable of cross-linking, that is, for bonding to Q.

Cross-linking agents in the sense of $V^2$, preferably have at least two reactive structures capable of alkylation. The necessary bonding to the siloxane chain is done by hydrosylilation via an additional unsaturated structure. Suitable, commercially available starting materials are preferably derivatives of polyhydroxy compounds, for example, monoallylglycerol or monoallyltrimethylol propane. These can be reactively functionalized by esterification with halogen carboxylic acids or esterifications with epichlorohydrine.

Derivatives of this type which are not available commercially are accessible through two-stage synthesis. First, there is the alkaline catalyzed monoetherification of the polyhydroxy compound with the corresponding unsaturated alkenyl halide or alkinyl halide (Organikum, Organisch-chemisches Grundpraktikum [=Organikum, Basic Practice of Organic Chemistry], 17th edition, VEB Deutscher Verlag der Wissenschaften, Berlin, 1988, pp. 196-199). Subsequently, the intermediate product with halogen carboxylic acids or acid chlorides or anhydrides is esterified. Alternatively, etherification is done with epichlorohydrine under alkaline conditions.

An advantageous variant follows from the use of unsaturated carboxylic acids, their carboxylic acid halides, or anhydrides, e.g. undecene carboxylic acid, as starting material. First, a monoesterification is done with the corresponding polyhydroxy compound. Subsequently, the intermediate product is esterified with halogen carboxylic acids or acid chlorides or anhydrides. Alternatively, etherification is done with epichlorohydrine under alkaline conditions.

An additional advantageous variant follows from the use of unsaturated diols, for example butene diol or butine diol. These can be directly esterified with halogen carboxylic acids or etherified with epichlorohydrine.

Structural units which correspond to $V^{1\nu}$(-Q-), can, for example, be built by the use of polyfunctional amines. On the one hand, it is preferred to use trifunctional and higher functional primary and secondary amines. Examples are the Jeffamines of the T-series (Huntsman Corp.).

Monosecondary ditertiary triamines, for example, N,N,N',N'-tetramethyl diethylene triamine or N,N,N',N'-tetramethyl dipropylene triamine are also suitable. Furthermore, advantageously usable are the commercially available tritertiary or tetratertiary amines such as N,N,N',N',N''-pentamethyl diethylene triamine, N,N,N',N',N''-pentamethyl dipropylene triamine, N,N-bis-(3-dimethylaminopropyl-)N-isopropanolamine, and tris-(3-dimethylaminopropyl)amine (Huntsman Corp.).

Independently of the choice of the branching structural units, the total stochiometry, which can be described in essence by Σ (primary+secondary+tertiary N):Σ(linker precursor forming reactive groups to $V^2$—+reactive groups to $V^1$)=1:1, is not changed. Cross-linking agents based on amino groups or other reactive groups replace equivalent amounts of functional groups of structures not capable of cross-linking.

The choice of the branching structural unit essentially decides at what point in time the cross-linking locations in the molecule can be introduced.

The quaternization reactions are preferably carried out in water, polar organic solvents, or mixtures of both components. Suitable are, for example, alcohols, especially methanol, ethanol, i-propanol, and n-butanol, glycols such as ethylene glycol, diethylene glycol, triethylene glycol, and the methyl ethers, ethyl ethers, and butyl ethers of said glycols. 1,2-propylene glycol and 1,3-propylene glycol, ketones such as acetone and methyl ethyl ketone, esters such as ethyl acetate, butyl acetate, and 2-ethyl-hexylacetate, ethers such as tetrahydrofuran, and nitro compounds such as nitromethane. The choice of solvent is directed essentially toward the solubility of the reaction partners and the reaction temperature strived for.

The reactions are carried out in the range from 20° C. to 130° C., preferably 40° C. to 100° C.

The invention relates furthermore to the use of the branched polyorganosiloxane polymers in cosmetic formulations, in washing agents, or for surface treatment of substrates.

Along with this the products according to the invention, which, in themselves, combine the softening properties of siloxane structures and the tendency of quaternary ammonium groups to combine for adsorption on the surfaces of negatively charged solid bodies, can be used in cosmetic formulations for skin and hair care, in polishes for the treatment and finishing of hard surfaces, in formulations for drying automobile, and other, hard surfaces after machine washing, for the finishing of textiles and textile fibers, particularly permanent hydrophilic softeners, as separate softeners after the washing of textiles in formulations based on anionic/nonionogenic surfactants for washing textiles, as well as an aid to ironing and means to prevent or restore creases in textiles.

The invention furthermore relates to compositions containing at least one of the branched polyorganosiloxane polymers together with at least one additional constituent customary for the composition such as cosmetic compositions, washing agent compositions, polishes, shampoos, aids to ironing, or crease-free finishes.

The use of the branched polyorganosiloxane polymers according to the invention leads in application in the hair cosmetics field to favorable effects with regard to setting, sheen, hold, body, volume, regulation of moisture, color retention, protection against the effects of the environment (UV, salt water, etc.), resiliance, antistatic properties, ability to dye, ability to comb, and so on. That means the quaternary polysiloxane compounds can be used preferentially in cosmetic and hair care formulations according to WO 02-10257.

EXAMPLES

Example 1

12.9 g of deionized water, 86.8 g of 2-propanol, 1.02 g (17 mmol) of acetic acid, 3.4 g (17 mmol) of lauric acid, 2.2 g (25.68 mmol of N) of N,N,N',N'-tetramethylhexane diamine, 2.15 g (6.8 mmol of N) of an amine of the composition

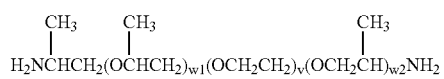

with $w1+w2=2.5$ and $v=8.5$ and 0.14 g (1.53 mmol of methyl-substituted N) of tris-(3-dimethylaminopropyl)amine are mixed and heated to 50° C. In the clear solution 90.8 g (34 mmol of epoxygroups) of an epoxysiloxane of average composition

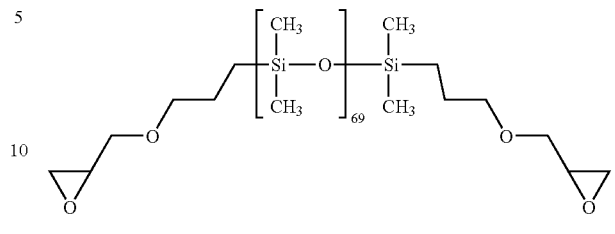

are added dropwise and the reaction solution heated for 9 hours at 82° C. After cooling, 197.5 g of a turbid, gray liquid is obtained. The polymer contained therein contains the following structural elements

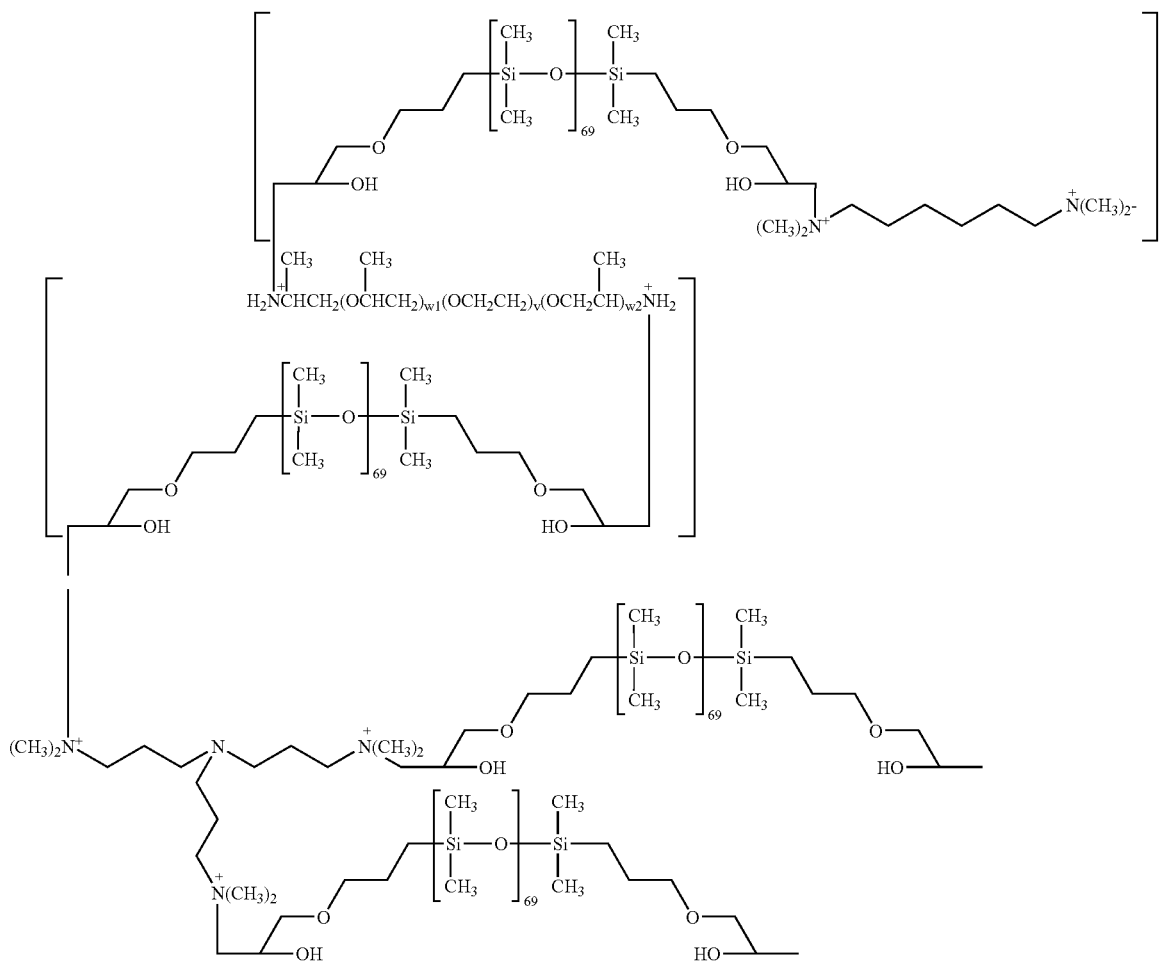

$(CH_3(CH_2)_{10}COO-$     $CH_3COO-$     $w1+w2=2.5$     $v=8.5$

Example 2

12.5 g of deionized water, 87 g of 2-propanol, 1.02 g (17 mmol) of acetic acid, 3.4 g (17 mmol) of lauric acid, 2.34 g (27.2 mmol of N) of N,N,N',N'-tetramethylhexane diamine, 1.67 g (5.28 mmol of N) of an amine of the composition

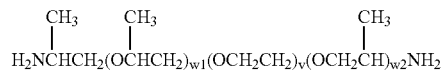

with $w1+w2=2.5$ and $v=8.5$ and 0.63 g (1.53 mmol of N) of a 40% solution of an amine of the composition

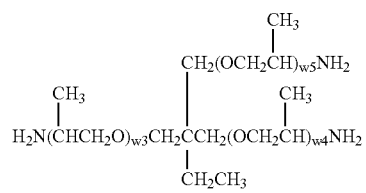

with $w3+w4+w5=5-6$ are mixed and heated to 50° C. In the clear solution 90.8 g (34 mmol of epoxy groups) of an epoxysiloxane of average composition

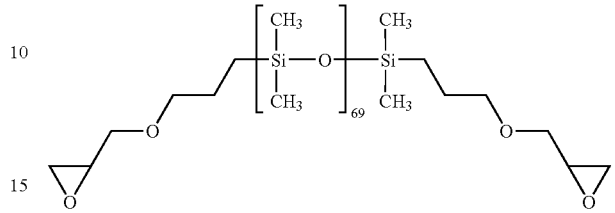

are added dropwise and the reaction solution heated for 10 hours at 82° C. After cooling, 197 g of a turbid, gray liquid is obtained. The polymer contained therein contains the following structural elements

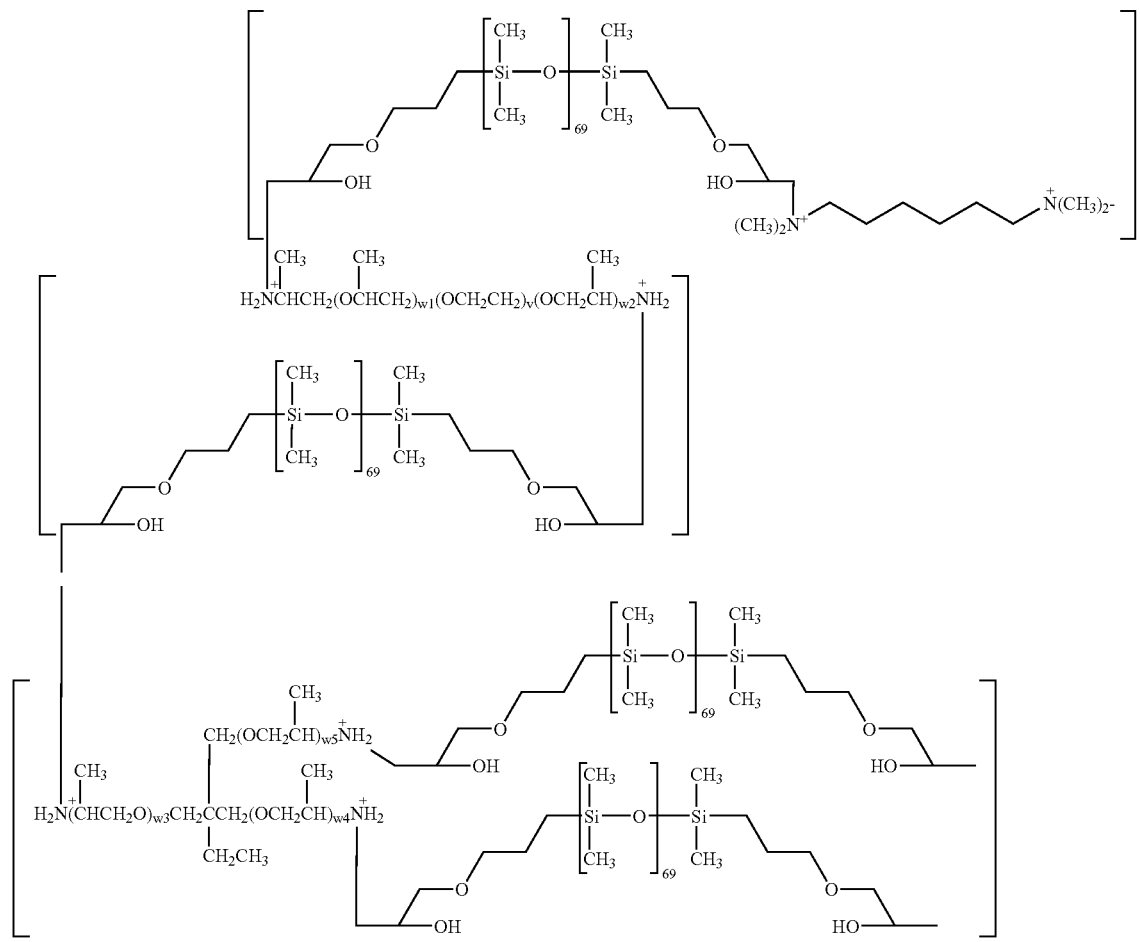

Example 3

3a) 24 g of deionized water, 6 g of concentrated HCl, and 134 g (1 mol) of tetramethyldisiloxane are mixed at room temperature and stirred. In a period of time of 20 minutes 88 g (0.33 mol) of tetraethoxysilane are added to the batch dropwise and the mixture stirred further for 30 minutes. After phase separation, 158 g of an oil phase can be taken off. This is dried over 20 g of Na$_2$SO$_4$ and subsequently fractionated by distillation. 71 g of a colorless liquid in the boiling range 79-83° C./16 mmHg are obtained. According to gas chromatography analysis it contains 89.7% QM$^H_4$.

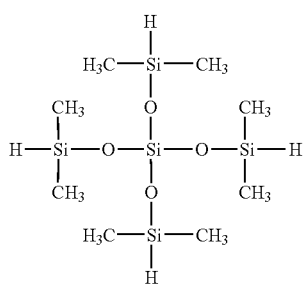

3b) 91 g (0.8 mol) of allylglycid ether are presented under nitrogen at room temperature. After heating to 90° C. 0.15 g of 1% H$_2$PtCl$_6$ in 2-propanol are first added dropwise and subsequently 50 g (0.52 mol of SiH) of QM$^H_4$ are added dropwise. The batch is heated for 3 hours at 135° C. Subsequently, all the components volatile up to 150° C./5 mmHg are removed. 107 g of an oily liquid are obtained

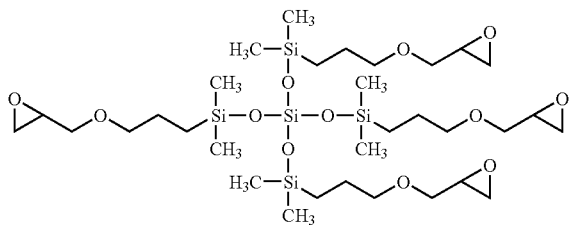

3c) 3.5 g of deionized water, 50 g of 2-propanol, 0.27 g (4.47 mmol) of acetic acid, 0.89 g (4.46 mmol) of lauric acid, 0.615 g (7.14 mmol of N) of N,N,N',N'-tetramethylhexane diamine, 0,12 g (0.89 mmol) of a 45% aqueous trimethylamine solution, and 0.95 g (0.89 mmol of N) of an amine of the composition

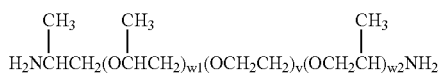

with $w1+w2=6$ and $+v39$ are mixed and heated to 50° C. In the clear solution 50 g (4.12 mmol of epoxy groups) of an epoxysiloxane of average composition

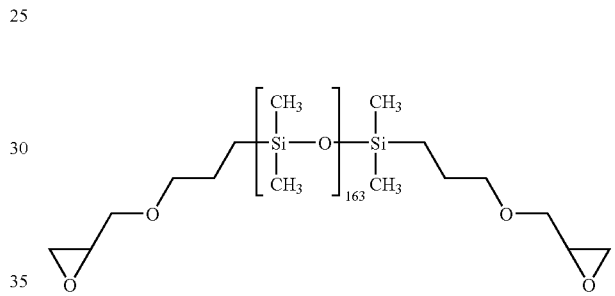

and 0.16 g (0.8 mmol) of the silicon-containing cross-linking agent according to 3b are added dropwise and the reaction mixture heated for 10 hours at 82° C. 97.7 g of a slightly yellow two-phase liquid are obtained which on cooling becomes highly viscous. The polymer found therein contains the following structural elements

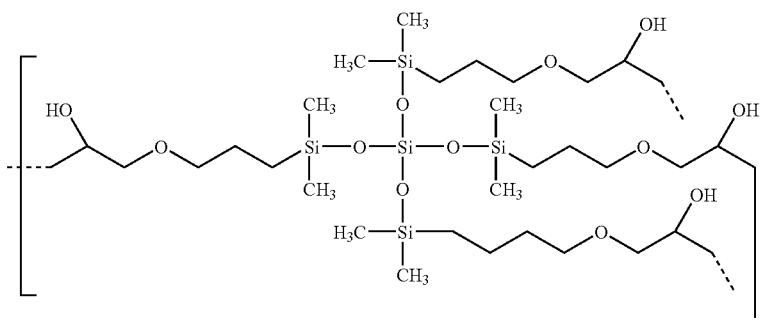

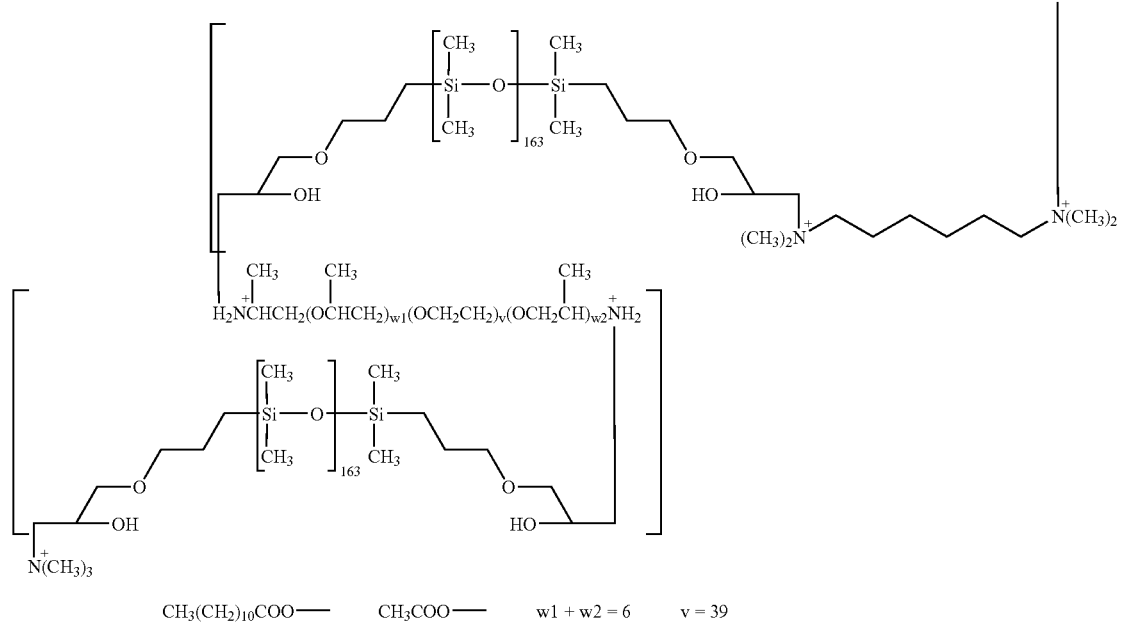

$CH_3(CH_2)_{10}COO^-$   $CH_3COO^-$   w1 + w2 = 6   v = 39

Example 4

4a) 238 g (2.24 mmol) of diethylene glycol are presented under nitrogen at room temperature. Under intensive stirring 558 g (4.93 mol) of chloroacetic acid chloride are added dropwise within one hour. During the dropwise addition the temperature increased to 82° C. and an intensive HCl development sets in. After completion of the dropwise addition the batch is heated at 130° C. for 30 minutes. Subsequently all the components boiling up to 130° C./20 hPa are distilled off. 566 g of a pale yellow oil of the composition

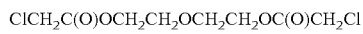

are obtained.

The ester's purity determined by gas chromatography is 99.2%.

$^{13}$C-NMR:

| Substructure | shift (ppm) |
| --- | --- |
| Cl$\underline{C}$H$_2$— | 40.7 |
| ClCH$_2$—$\underline{C}$(O)— | 167.1 |
| ClCH$_2$—C(O)—O$\underline{C}$H$_2$— | 65.2 |
| ClCH$_2$—C(O)—OCH$_2$$\underline{C}$H$_2$— | 68.6 |

4b) 373 g (3.3 mmol) of chloroacetic acid chloride are presented under nitrogen at room temperature. Under intensive stirring 92.1 g (3 mol of OH) of glycerin are added dropwise within 30 minutes, where the batch temperature rises from 24° C. to 100° C. There is more stirring for 1 hour at 100° C. Subsequently all the components boiling up to 100° C./30 mm Hg are removed. 341 g of a clear, yellow-brown, viscous liquid are obtained.

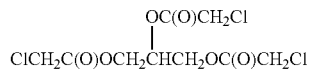

4c) 2.5 g of deioinized water, 10 g of 2-propanol, 4.5 g (22.5 mmol) of lauric acid, and 2.15 g (24.96 mmol of N) of N,N,N',N'-tetramethylhexane diamine are mixed and heated to 50° C. To the clear solution a mixture of 37.15 g (11.24 mmol of epoxy groups) of a siloxane of the structure

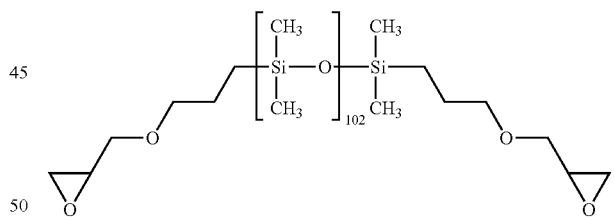

and 60.53 g (111.24 mmol of epoxy groups) of a siloxane of the structure

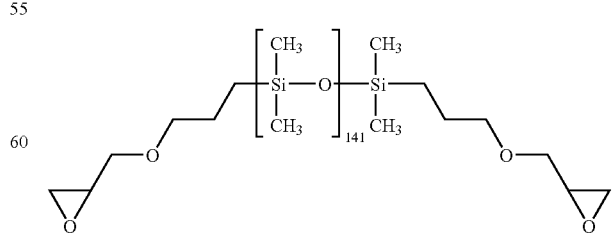

and 0.16 g (1.26 mmol of CL) of the diethylene glycol-based ester according to 4a) and 0.14 g (1.26 mmol of Cl) of the glycerin-based ester according to 4b) are added. The batch is heated for 6 hours to reflux temperature. After cooling 106 g of a clear amber-colored solution are obtained. The polymer found therein contains the following structural elements 2-propanol and 1.8 g (30 mmol) of acetic acid are added. After heating of the batch to 50° C. within 30 minutes 194.1 g (60 mmol of epoxy groups) of an epoxysiloxane of the average composition

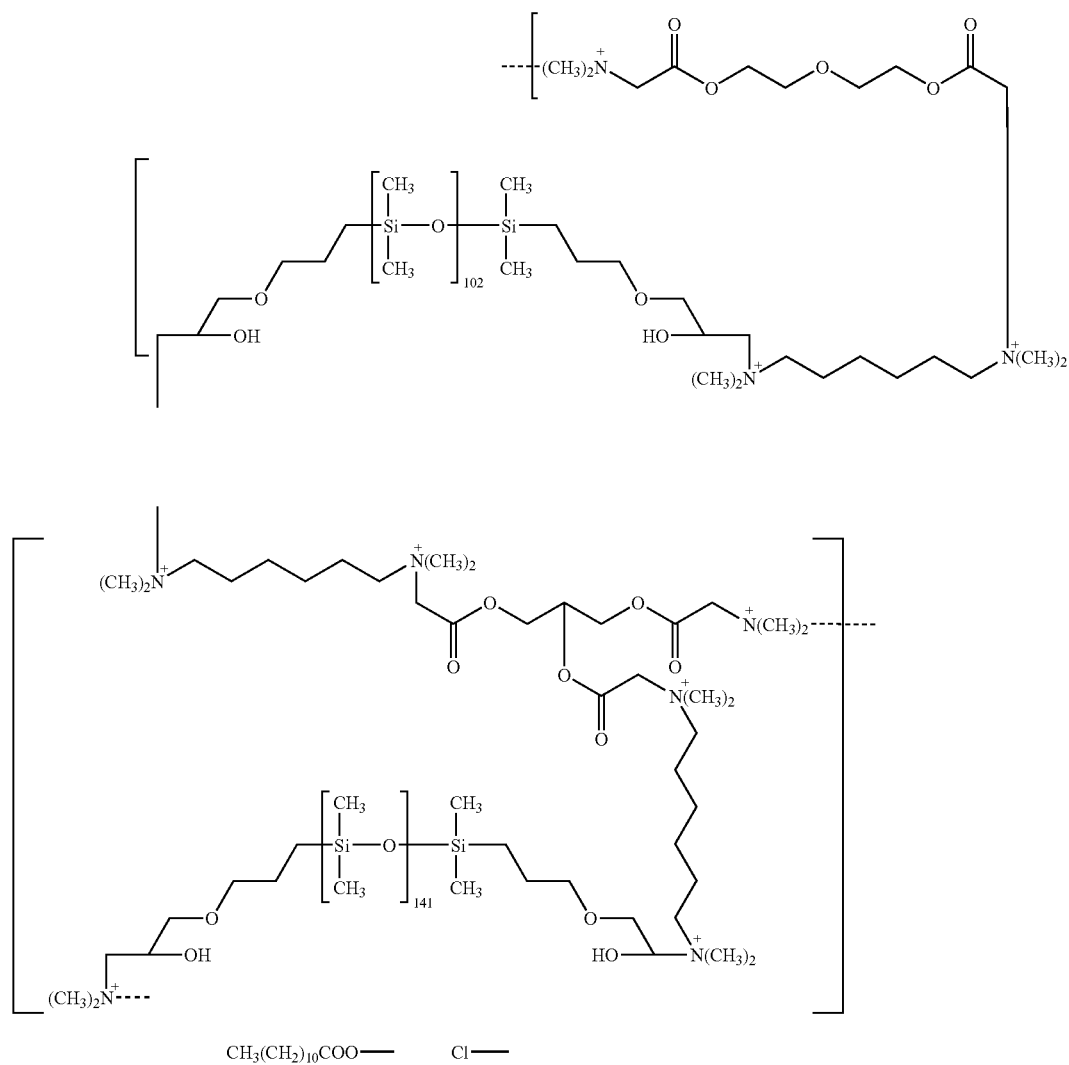

Example 5 (according to WO 02-010259; not according to the invention). In a 1-liter three neck flask 24 g of water and 4.18 g (48 mmol of tertiary amino groups) of N,N,N',N'-tetramethyl-1,6-hexane diamine and 12.77 g (12 mmol of primary amino groups) of an alkylene oxide derivative available under the trade name Jeffamin® ED 2003 of the structure

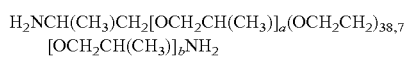

with a+b=6 are presented at room temperature. Within 5 minutes 12.0 g (30 mmol) of dodecanic acid in the form of a 50% solution in and 30 ml of 2-propanol are added dropwise. The yellow, turbid mixture is heated for 6 hours to reflux temperature. After removing all of the components volatile up to 100° C./2 mmHg in vacuum 209 g of a beige, turbid material of the structure

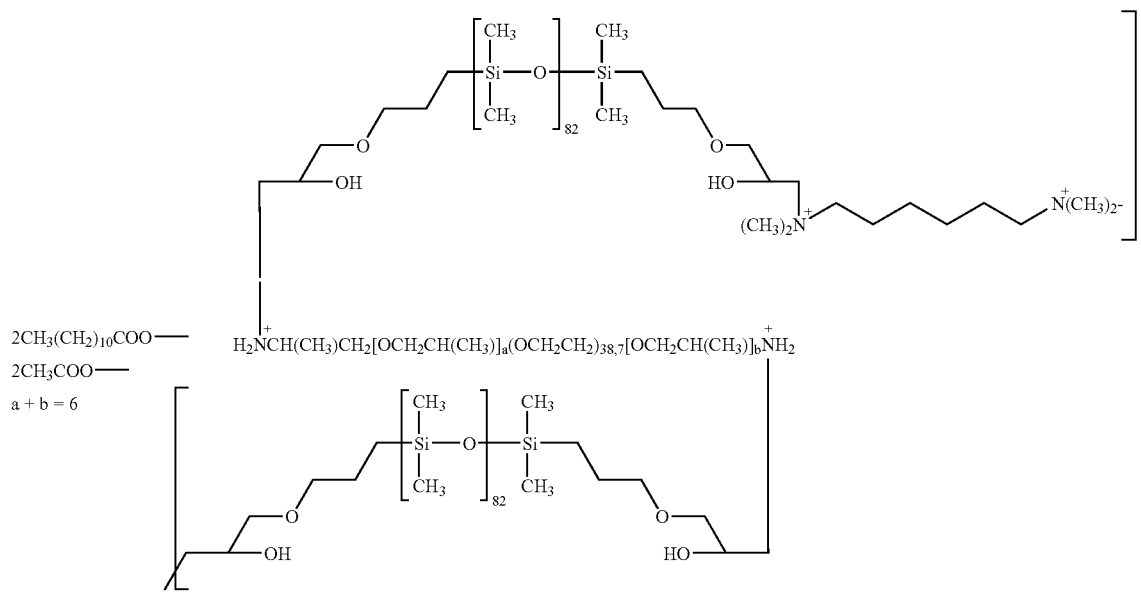

are obtained.

Example 6

To demonstrate the suitability as a softener 2.2 kg of commercially available terry cloth hand towels are washed with 45 g of Persil Megaperls® at 95° C. In the 3$^{rd}$ rinse cycle effectively 10 g of the softener according to the invention according to Example 1 and 2 as well as the softener not according to the invention according to Example 5 are added in microemulsion. As a reference, a batch of terry cloth hand towels is rinsed without softener. After the rinsing process, the hand towels are divided. One portion is subjected to linen drying while a second portion is subjected to the program "cabinet drying" in a dryer.

The terry cloth hand towels were evaluated by 6 test subjects where a sequence with increasing softness was to be developed. The hardest hand towel was evaluated with 1 point, while the softest hand towel received 4 points.

| Softener | Linen drying | Dryer | Note Ø |
|---|---|---|---|
| Example 1 | 3.2 | 3.8 | 3.5 |
| Example 2 | 3.6 | 2.6 | 3.1 |
| Example 5 (not inventive) | 2.2 | 2.6 | 2.4 |
| Reference (without softener) | 1 | 1 | 1 |

It can be recognized that the materials cross-linked according to the invention according to Examples 1 and 2 were clearly evaluated better than the material not according to the invention and not cross-linked according to Example 5.

The invention claimed is:
1. Branched polyorganosiloxane polymer containing at least one group of the structure

at least one group of the structure

at least one group of the structure

as well as at least one branching unit which is selected from the group consisting of S$^v$ and V$^v$,
where
   groups V are connected to groups Q and S,
   groups Q are not connected to groups S
   the groups S, S$^v$, V, V$^v$, and Q in a polymer molecule can be the same or different
and where

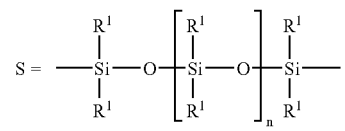

wherein
R$^1$ can be the same or different and is selected from the group consisting of: C$_1$ to C$_{22}$ alkyl, fluoro(C$_1$-C$_{10}$)alkyl and C$_6$-C$_{10}$ aryl, and n=0 to 1000,
S$^v$ is a three or higher valent organopolysiloxane unit,
Q is a divalent organic group containing at least one ammonium group,
V represents a divalent, straight-chain, cyclic or branched, saturated, unsaturated, or aromatic hydrocarbon group with up to 1,000 carbon atoms which optionally contains one or more groups selected from the group consisting of —O—, —NH—, —NR¹—, wherein R¹ is defined as above, —C(O)—,

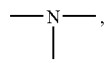

-and —C(S)—, and which, optionally, is substituted with one or more hydroxyl groups, $V^v$ represents a trivalent or higher valent, straight-chain, cyclic or branched, saturated, unsaturated, or aromatic hydrocarbon group with up to 1000 carbon atoms which optionally contains one or more groups selected from the group consisting of —O—, —NH—, —NR¹—, wherein R¹ is defined as above,

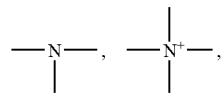

—C(O)—, and —C(S)—, and which, optionally, is substituted with one or more hydroxyl groups, and wherein the positive charges resulting from the ammonium group are neutralized by organic or inorganic acid anions and their acid addition salts.

2. Branched polyorganosiloxane polymer according to claim 1, wherein the divalent organic group Q containing at least one ammonium group is selected from the group consisting of

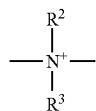

a quaternized imidazole unit of the structure

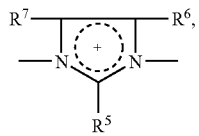

a quaternized pyrazole unit of the structure

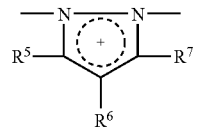

where $R^5$, $R^6$, and $R^7$ can be the same or different and are selected from the group consisting of H, halogen, hydroxyl group, nitro group, cyano group, thiol group, carboxyl group, alkyl group, monohydroxyalkyl group, polyhydroxyalkyl group, thioalkyl group, cyanoalkyl group, alkoxy group, acyl group, acetyloxy group, cycloalkyl group, aryl group, alkylaryl group, and groups of the type —NHR$^W$ in which R$^W$ means H, alkyl group, monohydroxyalkyl group, polyhydroxyalkyl group, acetyl group, ureido group, and the groups $R^6$ and $R^7$ with the carbon atoms binding them to the imidazole ring, or two of the groups $R^5$, $R^6$, and $R^7$ with the carbon atoms binding them to the pyrazole ring, optionally form aromatic five-element to seven-element rings, a diquaternized piperazine unit of the structure

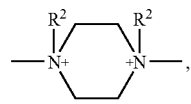

a monoquaternized piperazine unit of the structure

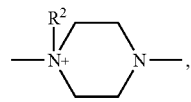

a monoquaternized piperazine unit of the structure

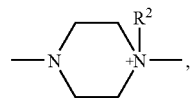

a diquaternized unit of the structure

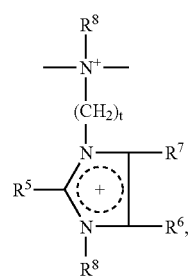

a monoquaternized unit of the structure

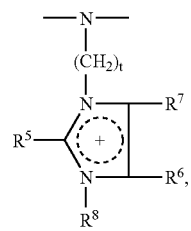

a monoquaternized unit of the structure

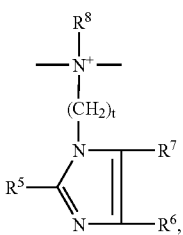

a diquaternized unit of the structure

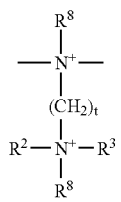

a monoquaternized unit of the structure

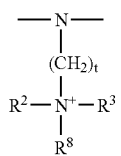

a monoquaternized unit of the structure

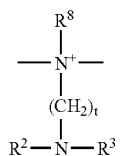

where t=2 to 10 and $R^2$ and $R^3$ =H or represents a monovalent, straight-chain, cyclic or branched, saturated, unsaturated, or aromatic hydrocarbon group with up to 40 carbon atoms which optionally contain one or more groups selected from the group consisting of —O—, —NH—,

—C(O)—, and —C(S)—, and which, optionally, can be substituted with one or more hydroxyl groups, where $R^2$ and $R^3$ can be the same or different, or $R^2$ and $R^3$, together with the positively charged nitrogen atom, form a five-element to seven-element heterocycle which, in given cases, can have in addition one or more nitrogen, oxygen, and/or sulfur atoms, $R^8$ has the meaning of $R^2$, where $R^8$ and $R^2$ can be the same or different.

3. Branched polyorganosiloxane polymer according to claim 1, wherein

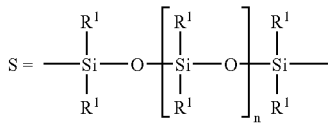

where
$R^1$ is selected from the group consisting of methyl, ethyl, trifluoropropyl, and phenyl, and n is a number from 0 to 350.

4. Branched polyorganosiloxane polymer according to claim 1, wherein V represents a divalent, straight-chain, cyclic or branched, saturated, unsaturated, or aromatic hydrocarbon group with up to 400 carbon atoms which optionally contains one or more groups selected from the group consisting of —O—, —NH—, —NR$^1$—, where $R^1$ is defined as above, $$-\underset{|}{N}-,$$

—C(O)—, and —C(S)—, which are optionally substituted with one or more hydroxyl groups.

5. Branched polyorganosiloxane polymer according to claim 1, comprising repeating units of the structure

where Q and S are defined as above, $V^1$ and $V^2$ have the meaning of V but are different from one another.

6. Branched polyorganosiloxane polymer according to claim 1, comprising repeating units of the structure

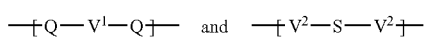

where Q nd S are defined as above, and $V^1$ and $V^2$ have the meaning of V but are different from one another.

7. Branched polyorganosiloxane polymer according to claim 5 or 6 wherein —$V^1$— is selected from the group, consisting of —$R^9$— where $R^9$ represents a divalent, saturated or singly or multiply unsaturated, straight-chain or branched, hydrocarbon group with two to 25 carbon atoms selected from the group, consisting of —(CH$_2$)$_u$C(O)O—[(CH$_2$CH$_2$O)$_q$—(CH$_2$CH(CH$_3$)O)$_r$]—C(O)(CH$_2$)$_u$—

—(CH$_2$)$_u$C(O)O—R$^9$—O—C(O)(CH$_2$)$_u$—, where $R^9$ is defined as previously, —(CH$_2$)$_u$—R$^{10}$—(CH$_2$)$_u$—, where R10 is an aromatic group, —[CH$_2$CH$_2$O]$_q$—[CH$_2$CH(CH$_3$)O]$_r$—CH$_2$CH$_2$—, —CH(CH$_3$)CH$_2$O[CH$_2$CH$_2$O]$_q$—[CH$_2$CH(CH$_3$)O]$_r$—CH$_2$CH(CH$_3$)—

—CH$_2$CH(OH)CH$_2$—,

—CH$_2$CH(OH)(CH$_2$)$_2$CH(OH)CH$_2$—,

—CH$_2$CH(OH)CH$_2$OCH$_2$CH(OH)CH$_2$OCH$_2$CH(OH)CH$_2$— and

—CH$_2$CH(OH)CH$_2$O—[CH$_2$CH$_2$O]$_q$—[CH$_2$CH(CH$_3$)O]$_r$—CH$_2$CH(OH)CH$_2$— where
u is from 1 to 3,
q is from 0 to 200,
r is from 0 to 200, and
q+r>0.

8. Branched polyorganosiloxane polymer according to claim 5 or 6, comprising a group of the structure $$-\!\!\left[V^2\!-\!S\!-\!V^2\right]\!-,$$

where S is defined as above and —$V^2$— is selected from the group consisting of:

—(CH$_2$)$_3$OCH$_2$CHCH$_2$—           —(CH$_2$)$_3$OCH$_2$CH—
                    |                                    |
                    OH                                  CH$_2$OH

—(CH$_2$)$_2$—[cyclohexyl with OH, CH$_3$]    —(CH$_2$)$_2$—[cyclohexyl with OH]

—CH$_2$CH—[cyclohexyl with OH, CH$_3$, CH$_3$]
     |
     CH$_3$

—CH$_2$CH—[cyclohexyl with CH$_3$, CH$_3$, OH]
     |
     CH$_3$

—(CH$_2$)$_2$—, —(CH$_2$)$_3$—, —(CH$_2$)$_4$—,
—(CH$_2$)$_5$—, —(CH$_2$)$_6$—,
—CH=CHCH$_2$—, —CH=CHCH$_2$CH$_2$—,
—CH$_2$CH$_2$CH$_2$OC(O)CH$_2$—,
—CH$_2$CH$_2$CH$_2$OC(O)CH$_2$CH$_2$—,
—CH=CHCH$_2$OC(O)CH$_2$— und
—CH=CHCH$_2$OC(O)CH$_2$CH$_2$—.

9. Branched polyorganosiloxane polymer according to claim 1, wherein
$S^v$ is a trivalent or higher valent organopolysiloxane group which has at least three silicon atoms which are each connected to three or more groups V or $V^v$ via a bond to a carbon atom of the respective group V or $V^v$.

10. Branched polyorganosiloxane polymer according to claim 2, comprising a branching group of the formula $V^{1v}(-Q-)_x$, where $V^{1v}(-Q-)_x$ is a trivalent or higher valent group, where Q is defined as above, and x is a whole number of at least three, and where $V^{1v}$ is selected from the group consisting of:

$R^{11}$—[(CH$_2$CH$_2$O)$_v$(CH$_2$CH(CH$_3$)O)$_w$—CO—(CH$_2$)$_u$]$_{3-6}$—, where $R^{11}$ is a trivalent or hexavalent group which is derived from a polyol in which 3 to 6 hydroxyl-hydrogen atoms are substituted,
v and w are numbers from 0 to 200,
v+w≧0, and
u=1 to 3

$R^{11}$—[(CH$_2$CH$_2$O)$_v$(CH$_2$CH(CH$_3$)O)$_w$—CH$_2$CH(OH)CH$_2$]$_{3-6}$—, where $R^{11}$, v, and w are defined as above $$-(CH_2)_t-\overset{(CH_2)_t-}{\underset{(CH_2)_t-}{N^+}}-R^2,$$

where t is from 2 to 10 and $R^2$ is defined as above $$-(CH_2)_t-\overset{(CH_2)_t-}{\underset{(CH_2)_t-}{N^+}}-V^3,$$

where t is from 2 to 10 and $V^3$ is a partial structure which is derived from V or $V^v$, and, $$-(CH_2)_t-\overset{(CH_2)_t-}{\underset{V^3}{N^+}}-R^2,$$

where t is from 2 to 10 and $R^2$ and $V^3$ are defined as above.

11. Branched polyorganosiloxane polymer according to claim 10, wherein the polyol is selected from the group consisting of: glycerol, trimethylolpropane, pentaerythritol, sorbitol, and sorbitan.

12. Branched polyorganosiloxane polymer according to claim 1, comprising a branching group of the structure $V^{2v}$ which is connected to at least one group S or $S^v$ and where $V^{2v}$ is a trivalent or higher valent group which is selected from the group consisting of:

—(Z—)$_y$$R^{12}$[—CH$_2$CH$_2$O)$_v$(CH$_2$CH(CH$_3$)O)$_w$—CO—CH$_2$)$_u$]$_z$—, where $R^{12}$ is a trivalent or hexavalent group which is derived from a polyol in which 3 to 6 hydroxyl-hydrogen atoms are substituted, and Z is a divalent hydrocarbon group with up to 20 carbon atoms which optionally contains one or more groups selected from the group consisting of —O— and —C(O)—, which optionally are substituted with one or more hydroxyl groups, and where the group Z is bonded by one of its carbon atoms to a silicon atom of the groups S or $S^v$, v and w are numbers from 0 to 200,
v+w≧0,
u=1 to 3,
y=1 to 6,
z=0 to 5,
z+y=3 to 6, (—)$_m$$R^{13}$[—O(CH$_2$CH$_2$O)$_v$(CH$_2$CH(CH$_3$)O)$_w$—CO—CH$_2$)$_u$]$_n$—, where $R^{13}$ is a trivalent or hexavalent, saturated or unsaturated, linear, branched or cyclic hydrocarbon group with up to 10 carbon atoms, (—) represents a single bond to a silicon atom of the group S or $S^v$, v and w are numbers from 0 to 200,
v+w≧0,
u=1 to 3,
m=1 or 2,
n=1 to 5, and
m+n=3 to 6

$(-)_m R^{13}[-O(CH_2CH_2O)_v(CH_2CH(CH_3)O)_w-CH_2CH(OH)CH_2]_n-$, where m, $R^{13}$, v, w, and n are defined as above, $-(Z-)_y R^{12}[-(CH_2CH_2O)_v(CH_2CH(CH_3)O)_w-CH_2CH(OH)CH_2]_z-$, where Z, y, $R^{12}$, v, w, and z are defined as above.

13. Branched polyorganosiloxane polymer according to claim 1, wherein $S^v$ and $V^v$ are branching units and the molar ratio of the sum of the branching units $S^v$ and $V^v$ to the sum of the linear repeating units S, V, and Q is 0.001% to 20%.

14. Branched polyorganosiloxane polymer according to one of claims 9 to 13, where the molar ratio of $V^v$ to V is from 0.002% to 20%.

15. Branched polyorganosiloxane polymer according to claim 1, 2, 3, 4, 5, 6, 9, 10, 11, 12, or 13, where the molar ratio of $S^v$ to S is from 0.002% to 20%.

16. Process for the production of the branched polyorganosiloxane polymer of claim 1, comprising conversion of:
   a) at least one organic compound which has two amino groups and which optionally comprises a polyorganosiloxane group, with
   b) at least one organic compound which has two epoxy groups and which optionally comprises a polyorganosiloxane group, with
   c) at least one organic compound which has two halogen alkylcarbonyloxy groups and which optionally comprises a polyorganosiloxane group, as well as
   d) at least one branching compound containing at least three functionalities selected from the group consisting of amine, epoxy, or chloroalkylcarbonyloxy functional groups.
   wherein at least one of the compounds a) to d) contains a polyorganosiloxane group.

17. A cosmetic formulation, washing agent or formulation for the surface treatment of substrates comprising the branched polyorganosiloxane polymer of claim 1.

18. A shampoo, 2-in-1 shampoo, clear and turbid leave-on conditioner, hair rinse or pearl sheen formulation, setting gel, setting foam, setting aerosol, or hair-dyeing formulation, comprising the branched polyorganosiloxane polymer of claim 1.

* * * * *